United States Patent [19]
Kun et al.

[11] Patent Number: 5,652,260
[45] Date of Patent: Jul. 29, 1997

[54] ADENOSINE DIPHOSPHORIBOSE POLYMERASE BINDING NITROSO AROMATIC COMPOUND USEFUL AS RETROVIRAL INACTIVATING AGENTS, ANTI-RETROVIRAL AGENTS AND ANTI-TUMOR AGENTS

[75] Inventors: Ernest Kun, Mill Valley; Jerome Mendeleyev, San Francisco, both of Calif.; William C. Rice, Frederick, Md.

[73] Assignee: Octamer, Inc., Mill Valley, Calif.

[21] Appl. No.: 488,425

[22] Filed: Jun. 7, 1995

Related U.S. Application Data

[60] Division of Ser. No. 87,566, Jul. 2, 1993, which is a continuation-in-part of Ser. No. 965,541, Nov. 2, 1992, Pat. No. 5,516,941, which is a continuation-in-part of Ser. No. 893,429, Jun. 4, 1992, abandoned, which is a continuation-in-part of Ser. No. 780,809, Oct. 22, 1991, abandoned.

[51] Int. Cl.$^6$ .............. C07C 231/08; A61K 31/165; A61K 31/47; C07D 217/22
[52] U.S. Cl. .............. 514/457; 564/166; 564/163; 564/164; 514/619; 514/620; 514/617; 514/309; 546/141; 549/288
[58] Field of Search .............. 514/457, 619, 514/620, 617, 309; 564/166, 163, 164; 546/141

[56] References Cited

FOREIGN PATENT DOCUMENTS

| 371 560 A3 | 6/1992 | European Pat. Off. |
| 20262758 | 6/1971 | France . |
| 3-227923 | 1/1990 | Japan . |
| 2 244 646 | 11/1991 | United Kingdom . |
| WO89/07441 | 8/1989 | WIPO . |
| WO89/07939 | 9/1989 | WIPO . |
| WO91/04663 | 4/1991 | WIPO . |
| WO92/06687 | 4/1992 | WIPO . |
| WO93/07868 | 4/1993 | WIPO . |

OTHER PUBLICATIONS

Gorlick, J. of Virology, Apr. 1996, vol. 70 No. 4, pp. 2593–2597 1996
Gorelick, J of Virology, Jul. 1993, vol. 67, No. 7, pp. 4027–4036 1993
Cornille, Int J Peptide Protein Res, vol. 36, pp. 551–558, 1990.
South, Biochemistry, vol. 30, pp. 6342–6349, 1991.
Khan, J of Biological Chemistry, vol. 267, No. 10, Apr. 5, 1992, pp. 6689–6695 1992.
Khan, J of Bioligical Chemistry, vol. 269, No. 36, pp. 22538–22546, 1994.
Green, Proc Natl Acad Sci, vol 87, pp. 6403–6407, 1990.
1923, *J. Pharm. Soc. Jap.* 4981, pp. 615–628.
1923, *J. Pharm. Soc. Jap.*498:615–628.
Aldovini et al., 1990, "Mutations of RNA and protein sequences involved in human immunodeficiency virus Type I packaging result in production of noninfectious virus," *J. Virol.* 64:1920–1926.

Borek et al., 1984, "Inhibition of malignant transformation in vitro by inhibitors of poly(ADP–ribose) synthesis," *Proc. Natl. Acad. Sci. U.S.A.* 81:243–247.
Buki et al., 1991, "Destabilization of $Zn^{2+}$ coordination in ADP–ribose transferase (polymerizing) by 6–nitroso–1, 2–benzopyrone coincidental with inactivation of the polymerase but not the DNA binding function," *FEBS Lett*, 290:181–185.
Buki et al., 1991, "Inhibitor Binding of Adenosine Disphosphoribosyl Transferase to the DNA Primer Site of Reverse Transcriptase Templates," *Biochem. Biophys. Res. Commun.* 180:496–503.
Buki et al., 1991, "Destabilizaton of Zn(ll) coordination in poly (ADP–ribose) polymerase by 6–nitroso–1,2–benzopyrone coincidental with inactivation of the polymerase but not the DNA binding function," The Paul Mandel International Meeting of Poly (ADP–Ribosyl)ation Reactions, Abstract 22C May 30, 1991.
Casasfinet et al., 1993, "3–nitrosozenzamide (NOBA) reacts with the zinc–finger sequence of HIV–1 nucleocapsid protein (P7) and phage T4 gene 32 protein (GP32)," *Biophys. Journal* 64(2):A125, abstract.
Chuang et al., 1993, "Inhibition of the Replication of Native and 3'–azido–2',3'–dideoxy–thymidine (AZT)–resistant simian immunodeficiency virus (SIV) by 3–nitrosobenzamide," *FEBS Lett.* 326:140–144.
Cole et al., 1991, "Inhibition of HIV–1 IIIb Replication in AA–2 and MT–2 Cells in Culture By Two Ligands of Poly (ADP–RIBOSE) Polymerase; 6–Amino–1,2–Benzopyrone and 5–Iodo–6–Amino–1,2–Benzopyrone," *Biochem. Biophys. Res. Commun.* 180:504–514.
Elhardt et al., 1988 "Nitrosoimidazoles: highly bactericidal analogues of 5–nitroimidazole drugs," *J. Med. Chem.* 31:323–329.
Farzaneh et al., 1988, "ADP–ribosylation is involved in the integration of foreign DNA into *Nucleic Acids Res.* " 16:11319–11326.
Furlini et al., 1991, "Increased poly (ADP–ribose) polymerase activity in cells infected by human immunodeficiency virus type–1," *Microbiologica* 14(2):141–148.
Gorelick et al., 1988, "Point mutants and Moloney murine leukemia virus that fail to package viral RNA: Evidence for specific RNA recognition by a zinc finger–like protein sequence," *Proc. Natl. Acad. Sci. USA* 85:8420–8424.

(List continued on next page.)

*Primary Examiner*—C. Warren Ivy
*Assistant Examiner*—D. Margaret M. Mach
*Attorney, Agent, or Firm*—Albert P. Halluin; Pennie & Edmonds LLP

[57] ABSTRACT

The subject invention provides for novel compounds for inactivating viruses. These compounds include 6-nitroso-1, 2-benzopyrone, 3-nitrosobenzamide, 5-nitroso-1(2H)-isoquinolinone, 7-nitroso-1(2H)-isoquinolinone, 8-nitroso-1 (2H)-isoquinolinone. The invention also provides for compositions containing one or more of the compounds, and for methods of treating viral infections, cancer, infectious virus concentration with the subject compounds and compositions.

24 Claims, 25 Drawing Sheets

OTHER PUBLICATIONS

Gorelick et al., 1990, "Noninfectious Human Immunodeficiency Virus Type 1 Mutants Deficient in Genomic RNA", *J. Virol.* 64:3207–3211.

Gradwohl et al., 1990, "The second zinc-finger domain of poly(ADP-ribose) polymerase determines specificity for single-stranded breaks in DNA," *Proc. Natl. Acad. Sci. USA* 87:2990–2994.

Grosso & Pitot. 1984, "Modulation of C-MYC Expression in the HL-60 Cell Line," *Biochemistry* 119:473–480.

Hakam et al., 1987, "Catalytic Activities of Synthetic Octadeoxyribonucleotides as Coenzymes of Poly (ADP-ribose) Polymerase and the Identification of a New Enzyme Inhibitory Site," *FEBS Lett.* 212:73–78.

Henderson et al., 1981, "Primary Structure of the Low Molecular Weight Nucleic Acid–binding Proteins of Murine Leukemia Viruses," *Biol. Chem.* 256:8400–8406.

Ibne-Rasa et al., 1963, "o-Nitrosobenzamide. A Possible Intermediate in the von Richter Reaction," *J. Org. Chem.* 28:3240–3241.

Ikushima, T., 1990, "Bimodal induction of sister–chromatid exchanges by luminol, an inhibitor of poly(ADP-ribose) synthetase, during the S–phase of the cell cycle," *Chromosoma* 99:360–364.

Ito et al., 1953, "Coumarin Derivatives for Medicinal Purposes," *J. Pharm. Soc. Jap.* 73:351–355.

Kirsten et al., 1991, "Cellular Regulation of ADP-Ribosylation of Proteins IV. Conversion of Poly (ADP-Ribose) Polymerase Activity to NAD-glycohydrolase During Retinoic Acid–Induced Differentiation of HL60 Cells," *Experimental Cell Research* 194:1–8.

Kitagawa et al., 1958, "Coumarin Derivatives for Medicinal Purposes," *Chem. Abstr.* 52:188474c.

Kitigawa, Haruo, 1954, "Coumarin Derivatives for Medicinal Purposes," *J. Pharm. Soc. Jap.* 74:271–278.

Kitigawa & Iwaki, 1963, "Coumarin Derivatives for Medicinal Purposes," *Yakugaku Zasshi* 83:1124–1128.

Kokotos et al., 1986, "Synthesis and Study of Substituted Courmarins. A Facile Preparation of D.L–o–Tyrosine," *J. Heterocyclic Chem.* 23:87–92.

Kovacic et al., 1190, "Reduction potentials in relation to physiological activities of benzenoid and heterocyclic nitroso compounds: comparison with the nitro precursors," *Bioorganic Chemistry* 18:265–275.

Krasil'Nikov et al., 1991, "Inhibitors of ADP-ribosylation as antiviral drugs: Experimental study of the model of HIV infection," *Vopr. Virusol. (Russia)* 36(3):216–218.

Krasil'Nikov et al., 1991, *Chemical Abstracts* 115:222844k.

Kun et al., 1983, "Cell cycle–dependent intervention by benzamide of carcinogen–induced neoplastic transformation and in vitro poly(ADP-ribosyl)ation of nuclear proteins in human fibroblasts," *Proc. Natl. Acad. Sci. U.S.A.*, 80:7219–7223.

Lever et al., 1989, "Identification of a Sequence Required for Efficient Packaging of Human Immunodeficiency Virus Type 1 RNA into Virons". *J. Virol.* 63:4085–4087.

McClelland et al., 1987, "Products of the reductions of 2-nitroimidizoles," *J. Am. Chem. Soc.* 109:4308–4314.

Merchant et al., 1983, "Synthesis of Some Benzopyranocyclopentapyridine and Pyranoacridine Deriviatives," *Chem. Abstr.* 99:105153z.

Meric and Goff, 1989, "Characterization of Moloney Murine Leukemia Virus Mutants with Single–Amino–Acid Substitutions in the Cys–His Box of the Nucleocapsid," *J. Virol.* 63:1558–1568.

Milo et al., 1985, "Inhibition of carcinogen–induced cellular transformaton of human fibroblasts by drugs that interact with the poly(ADO–ribose) polymerase system," *FEBS Lett.* 179:332–336.

Mulcahy et al., 1989 "Cytotoxicity and glutathione depletion by 1–methyl–2–nitrosimidazole in human colon cancer cells," *Biochem. Pharm.* 38:1667–1671.

Nakayashu et al., 1988, "Deletion of transfected oncogenes from NIH 3T3 transformants by inhibtors of poly(ADP-ribose) polymerase," *Proc. Natl. Acad. Sci. U.S.A.* 85:9066–9070.

Noss et al., 1988, "Preparation, toxicity and mutagenicity of 1–methyl–2–nitrosoimidazole," *Biochem, Pharm.* 37:2585–2593.

Noss et al., 1989, "1–Methyl–2–nitrosoimidazole: cytotoxic and glutathione depleting capabilities," *Int. J. Radiation Oncology Biol. Phys.* 16:1015–1019.

Pearson et al., 1991, *Chemical Abstracts* 114 Col. 23803a.

Rao, et al., 1989, "Mercaptocoumarinoxazoles," *Chem. Abstr.* 111:232636a.

Rice et al., 1992, "Induction of endonuclease–mediated apoptosis in tumor cells by C–nitroso–substituted ligands of poly (ADP–ribose) polymerase," *Proc. Natl. Acad. Sci. USA* 89:7703–7707.

Rice et al., 1993, "Novel Zinc–Ejecting C–Nitroso Compounds Inhibit the Infectious and Expressive Phases of HIV–1 Life Cycle," *Journal of Cellular Biochemistry* S17E:22.

Rice et al., 1993, "Inhibition of HIV–1 infectivity by zinc–ejecting aromatic C–nitroso compounds," *Nature* 361:473–475.

Rice et al., 1993, "The site of antiviral action of 3–nitrosobenzamide on the infectivity process of HIV in human lymphocytes," *Proc. Natl. Acad. Sci. U.S.A.* 90(20):9721–9724.

Romano et al., 1983, "Inhibitors of ADP–ribosyl transferase suppress the mitogeni actions exerted by tumour promoters, but not those evoked by peptide mitogens, in primary neonatal rat hepatocytes," *Carcinogenesis* 9:2147–2154.

Seidel et al., 1975, "Oxidation of Aromatic Hydrazides," *Chemical Abstracts* 82 Col. 16505X.

Shell et al., 1991, *Chemical Abstracts* 116:193929e.

Shima et al., 1989, "Loss of the MYC gene amplified in human HL–60 cells after treatment with inhibitors of poly-(ADP–ribose) polymerase or with dimethyl sulfoxide," *Proc. Natl. Acad. Sci. U.S.A.* 86:7442–7445.

South et al., 1989, "113 Cd NMR Studies of a 1:1 Cd Adduct with an 18–Residue Finger Peptide from HIV–1 Nucleic Acid Binding Protein, p7," *J. Am. Chem. Soc.* 111:395–396.

South et al., 1990, "Zinc fingers and molecular recognition. Structure and Nucleic acid binding studies of an HIV zinc finger–like domain," *Biochem. Pharm.* 40:123–129.

Sreenivasulu et al., 1975, "Search for Physiologically Active Compounds," *Chem. Abstr.* 82:111917s.

Summers et al., 1990, "High–Resolution Structure of an HIV Fingerlike Domain via a New NMR–Based Distance Geometry Approach", *Biochemistry* 29:329–340.

Summers et al., 1992, "Nucleocapsid Zinc Fingers Detected in Retroviruses: Exafs Studies of Intact Viruses and the Solution–State Structure of the Nucleocapsid Protein from HiV–1," *Protein Science* 1(5):563–574.

Tseng et al., 1987, "Prevention of tumorigenesis of oncogene-transformed rat fibroblasts with DNA site inhibitors of poly(ADP-ribose) polymerase," *Proc. Natl. Acad. Sci. U.S.A.* 84:1107–1111.

Varghese et al., 1983, "Modification of guanine derivatives by reduced 2–nitroimidazoles," *Cancer Research* 43:78–82.

Waldman and Waldman, 1990, "Illegitimate and homologous recombination in mammalian cells: differential sensitivity to an inhibitor of poly(ADP-ribosylation)," *Nucleic Acids Res.* 18:5981–5988.

Wubbels et al., 1982, "Mechanism of Water–Catalyzed Photo–Isomerization of p–nitrobenzaldhyde,"*J. Org. Chem.* 47:4664–4670.

Yamagoe et al. 1991, "Poly (ADP–ribose) polymerase inhibitors suppress UV–induced human immunodeficiency virus type 1 gene expression at the posttranscriptional level," *Mol. and Cell. Biol.* 11(7):3522–3527.

INACTIVATION OF ADPRP BY NITROSO COMPOUNDS 855-2 CELLS IN FCS

H9 CELLS IN FCS

—●— ABP  —+— IABP  —◆— NO2BP  —☐— NOBP  —△— NOBA  —◇— NOQ

HL-60 CELLS IN FCS

CONCENTRATION OF COMPOUNDS (log uM)

K562 CELLS IN FCS

CONCENTRATION OF COMPOUNDS (log uM)

—ABP  —+—IABP  —✦—NO2BP  —▭—NOBP  —△—NOBA  —◇—NOQ

855-2 CELLS IN AGF

855-2 CELLS + LMW-BCGF

→ ABP  —+— IABP  —•— NO2BP  —□— NOBP  —△— NOBA  —◇— NOQ

INHIBITION OF DIFFERENT LEVELS OF PROLIF OF 855-2 CELLS BY NOBP OR NOBA (10 uM)

| | 1% FCS | 2.5% FCS | 5% FCS | 10% FCS |
|---|---|---|---|---|
| CELLS: | 4708 ±85 | 9900 ±79 | 14108 ±876 | 22992 ±1760 |
| +NOBP | 53 ±53 | 30 ±13 | 53 ±38 | 39 ±15 |
| +NOBA | 100 ±84 | 179 ±207 | 15 ±8 | 14 ±13 |

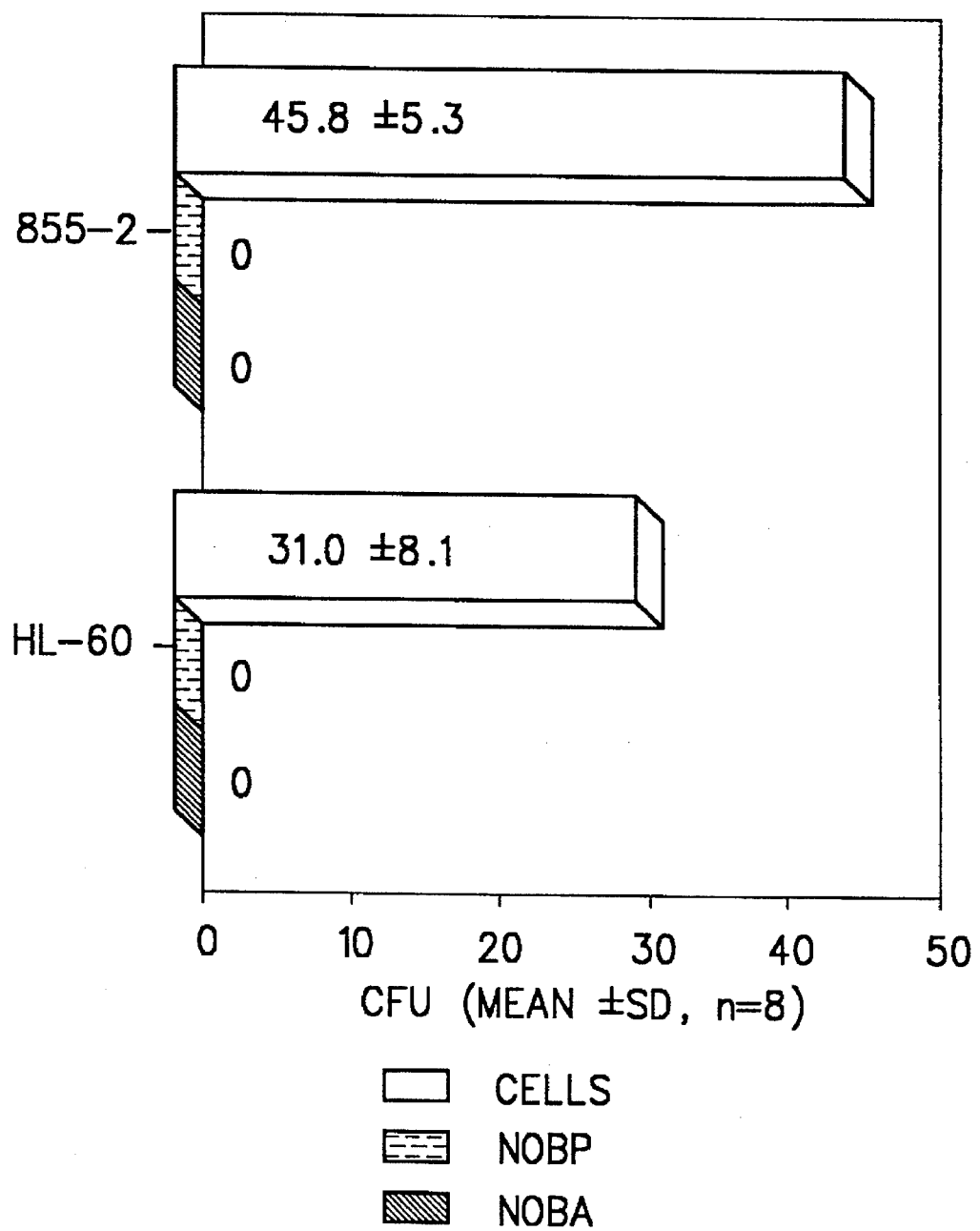

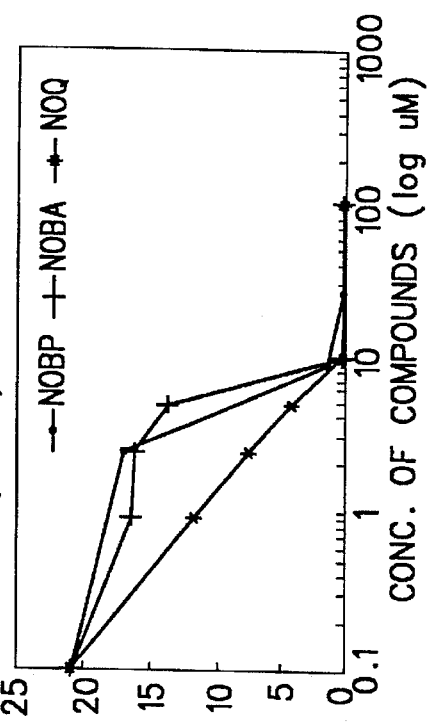
FIG. 6A EFFECT OF NITROSO COMPOUNDS ON GLIOBLASTOMA CELL LINE D 32
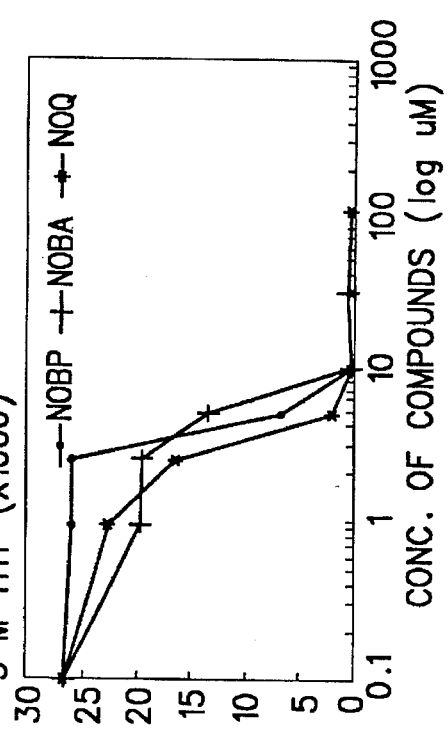
FIG. 6B EFFECT OF NITROSO COMPOUNDS ON GLIOBLASTOMA CELL LINE D 37
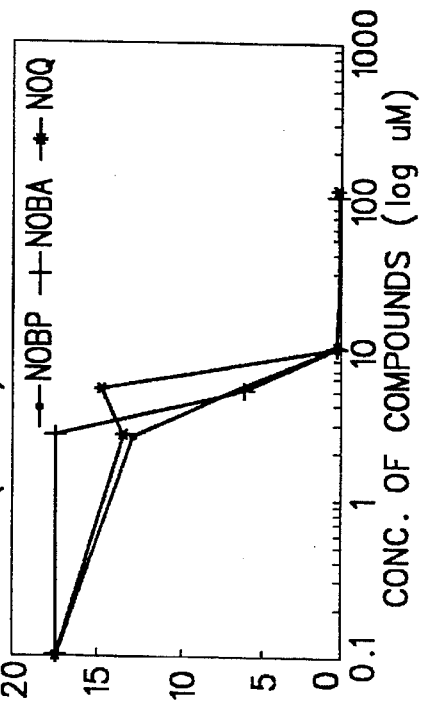
FIG. 6C EFFECT OF NITROSO COMPOUNDS ON GLIOBLASTOMA CELL LINE CRL 7712
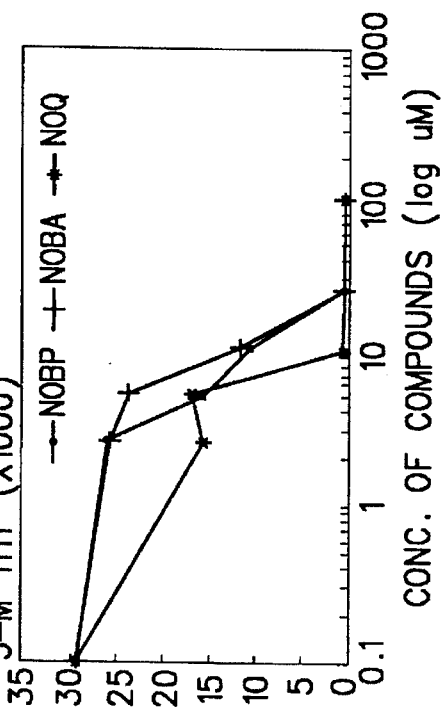
FIG. 6D EFFECT OF NITROSO COMPOUNDS ON MEDULLA CELL LINE 186

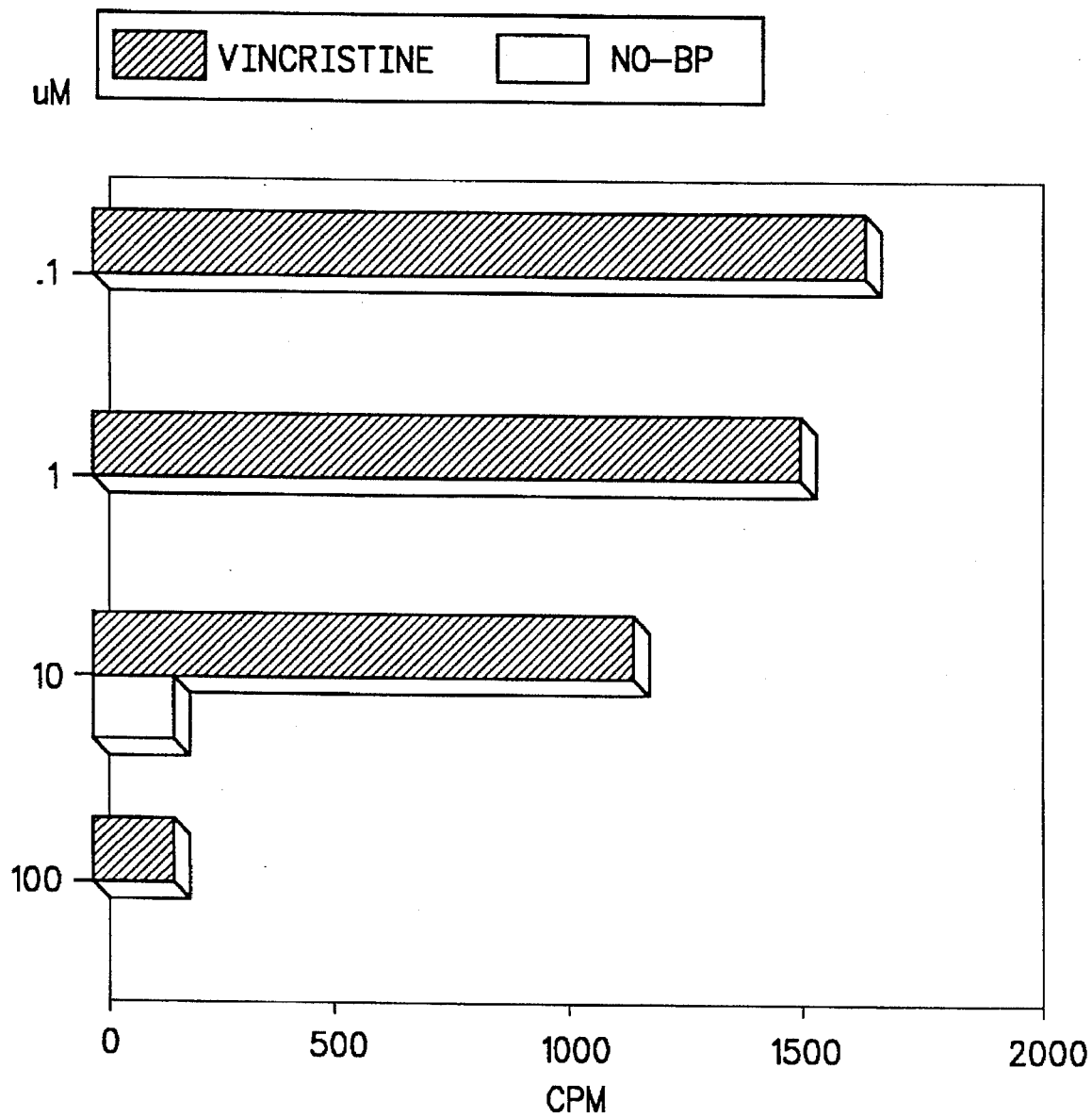

INHIBITION OF MDA-486 CELL LINE BY NITROSO AROMATIC COMPOUNDS

—381 bp

—162 bp

INHIBITION OF HIV-1 p24 PRODUCTION
BY NOBA

ADENOSINE DIPHOSPHORIBOSE POLYMERASE BINDING NITROSO AROMATIC COMPOUND USEFUL AS RETROVIRAL INACTIVATING AGENTS, ANTI-RETROVIRAL AGENTS AND ANTI-TUMOR AGENTS

CROSS REFERENCE TO RELATED APPLICATIONS

This is a division of application Ser. No. 08/087,566, filed Jul. 2, 1993; which is a CIP of application Ser. No. 07/965,541 filed Nov. 2, 1992, U.S. Pat. No. 5,516,991, which is a CIP of application Ser. No. 07/893,429 filed Jun. 4, 1992; which is a CIP of application Ser. No. 07/780,809 filed Oct. 22, 1991, both abandoned.

FIELD OF THE INVENTION

The present invention relates generally to the field of retroviral therapeutic and inactivating agents and their use in treating retroviral infections and cancers. More specifically it relates to those therapeutic and inactivating C-nitroso compounds which destabilize zinc fingers.

BACKGROUND OF THE INVENTION

The enzyme ADP-ribose transferase (ADPRT) (E.C.4.2.30) is a chromatin-bound enzyme located in the nucleus of most eukaryotic cells. The enzyme catalyzes the polymerization of the ADP-ribose moiety of nicotinamide adenine dinucleotide ($NAD^+$) to form poly (ADP-ribose). The polymer is covalently attached to various nuclear proteins, including the polymerase itself.

The many varied roles that ADP-ribosylation plays in cellular metabolism have made ADPRT a target for drugs essentially useful for combating neoplasia and viral infections. Numerous physiological activities have been detected for compounds that inhibit the polymerase activity of ADPRT. Such activities include a cell cycle dependent prevention of carcinogen-induced malignant transformation of human fibroblasts (Kun, E., Kirsten, E., Milo, G. E. Kurian, P. and Kumari, H. L. (1983) *Proc. Natl. Acad. Sci. USA* 80: 7219–7223), conferring also carcinogen resistance (Milo, G. E., Kurian, P., Kirsten, E. and Kun, E. (1985) *FEBS Lett.* 179: 332–336), inhibition of malignant transformation in hamster embryo and mouse C3H10T1/2 cell cultures (Borek, C., Morgan, W. F., Ong, A. and Cleaver, J. E. (1984) *Proc. Natl. Acad. Sci. USA* 81: 243–247), deletion of transfected oncogenes from NIH 3T3 cells (Nakayashu, M., Shima, H., Aonuma, S., Nakagama, H., Nagao, M. and Sugimara, T. (1988) *Proc. Natl. Acad. Sci. USA* 85: 9066–9070), suppression of the mitogenic stimulation of tumor promoters (Romano, F., Menapace, L. and Armato, V. (1983) *Carcinogenesis* 9: 2147–2154), inhibition of illegitimate DNA recombinations (Waldman, B. C. and Waldman, A. (1990) *Nucl. Acids Res.* 18: 5981–5988) and integration (Farzaneh, F., Panayotou, G. N., Bowler, L. D., Hardas, B. D., Broom, T., Walther, C. and Shall, S. (1988) *Nucl. Acids Res.* 16: 11319–11326), induction of sister chromatid exchange (Ikushima, T. (1990) *Chromosoma* 99: 360–364) and the loss of certain amplified oncogenes (Grosso, L. E. and Pitot, H. C. (1984) *Biochem. Biophys. Res. Commun.* 119: 473–480; Shima, H., Nakayasu, M., Aonums, S., Sugimura, T. and Nagao, M. (1989) *Proc. Natl. Acad. Sci. USA* 86: 7442–7445).

Compounds known to inhibit ADPRT polymerase activity include benzamide (Kun, E., Kirsten, E., Milo, G. E. Kurian, P. and Kumari, H. L. (1983) *Proc. Natl. Acad. Sci. USA* 80: 7219–7223), substituted benzamides (Borek, C., Morgan, W. F., Ong, A. and Cleaver, J. E. (1984) *Proc. Natl. Acad. Sci. USA* 81: 243–247; Romano, F., Menapace, L. and Armato, V. (1983) *Carcinogenesis* 9; 2147–2154; Farzaneh, F., Panayotou, G. N., Bowler, L. D., Hardas, B. D., Broom, T., Walther, C. and Shall, S. (1988) *Nucl. Acids Res.* 16: 11319–11326.; Grosso, L. E. and Pitot, H. C. (1984) *Biochem. Biophys. Res. Commun.* 119: 473–480; Shima, H., Nakayasu, M., Aonums, S., Sugimura, T. and Nagao, M. (1989) *Proc. Natl. Acad. Sci. USA* 86: 7442–7445), 3-aminonaphthylhydrazide (Waldman, B. C. and Waldman, A. (1990) *Nucl. Acids Res.* 18: 5981–5988), isoquinoline, quercetin, and coumarin (1,2-benzopyrone) (Milo, G. E., Kurian, P., Kirsten, E. and Kun, E. (1985) *FEBS Lett.* 179: 332–336). The anti-transforming and anti-neoplastic effect of 1,2 benzopyrone were demonstrated in vitro and in vivo (Tseng, et al., (1987) *Proc. Natl. Acad. Sci. USA* 84: 1107–1111).

Other known ADPRT polymerase activity inhibitors include 5-iodo-6-amino-1,2-benzopyrone as described in U.S. patent application Ser. No. 600,593, filed Oct. 19, 1990 entitled "Novel 5-Iodo-6-Amino-1,2-Benzopyrones and their Metabolites Useful as Cystostatic and Anti-Viral Agents" for use as anti-tumor and anti-viral agents. The cited patent discusses the possibility of using 5-iodo-6-nitroso-1,2-benzopyrone as an anti-tumor or anti-viral agent.

The 6-nitroso-benzopyrones have not been hitherto known or described. The only remotely related compounds found in the literature are 6-nitro-1,2-benzopyrone and 6-amino-1,2-benzopyrone (6-ABP) (*J. Pharm. Soc. Jap.*, 498: 615 (1923)) for which, only scarce medicinal evaluation has been reported. In particular, testing was done for sedative and hypnotic effects (*J. Pharm. Soc. Japan*, 73: 351 (1953); Ibid, 74: 271 (1954)), hypothermal action (Yakugaku Zasshi, 78: 491 (1958)), and antipyretic, hypnotic, hypotensive and adrenolytic action (Ibid, 83: 1124 (1963)). No significant application for any of these compounds has been described except for 6-ABP.

2-nitrosobenzamide (Irne-Rasa, K. M. and Koubek, E. (1963) *J. Org. Chem.* 28: 3240–3241), and 4-nitrosobenzamide (Wubbels, G. G., Kalhorn, T. F., Johnson, D. E. and Campbell, D. (1982) *J. Org. Chem.* 47: 4664–4670), have been reported in the chemical literature, but no commercial use of these isomers is known. Neither of these articles suggest the use of nitrosobenzamides as ADPRT inhibitors.

The anti-retroviral and anti-tumorigenic actions of substituted and unsubstituted 6-amino-1,2-benzopyrone and 5-iodo-6-amino-1,2-benzopyrone is the subject of copending U.S. patent applications Ser. No. 585,231 filed on Sep. 21, 1990 entitled "6-Amino-1,2-Benzopyrones Useful for Treatment of Vital Diseases" and Ser. No. 600,593 filed on Oct. 19, 1990 entitled "Novel 5-Iodo-6-Amino-1,2-Benzopyrones and Their Metabolites Useful as Cytostatic and Antiviral Agents", which are incorporated herein by reference.

The precursor molecule, 1,2-benzopyrone (coumarin), was shown to be an inhibitory ligand of adenosinediphosphoribosyl transferase (ADPRT), a DNA-binding nuclear protein present in all mammalian cells (Tseng, et al., (1987) *Proc. Nat. Acad. Sci. USA*, 84: 1107–1111).

Hakam, et al., *FEBS Lett.*, 212: 73 (1987) has shown that 6-amino-1,2-benzopyrone (6-ABP) binds specifically to ADRPT at the site that also binds to DNA, indicating that both 6-ABP and DNA compete for the same site on ADPRT.

Synthetic ligands of ADPRT inhibit DNA proliferation, particularly in tumorigenic cells, (Kirsten, et al., (1991) *Exp. Cell. Res.* 193: 1–4). Subsequently, these ligands were found to inhibit viral replication and are the subject of the copending U.S. patent application entitled "6-Amino-1-2-Benzopyrones useful for Treatment of Vital Diseases," Ser. No. 585,231, filed on Sep. 21, 1990 which is hereby incorporated by reference.

Retroviral nucleocapsid (NC) proteins and their respective gag precursors from all strains of known retroviruses contain at least one copy of a zinc-binding polypeptide sequence of the type $Cys-X_2-Cys-X_4-His-X_4-Cys$ (CCHC) (Henderson, et al., *Biol. Chem.* 256: 8400–8406 (1981)), i.e., a zinc finger domain. This CCHC sequence is essential for maintaining retroviral infectivity (Gorelick, et al., *Proc. Natl. Acad. Sci. USA* 85: 8420–8424 (1988), Gorelick, et al., *J. Virol.* 64: 3207–3211 (1990)), therefore, it represents an attractive target for retroviral chemotherapy. The HIV-1 gag proteins function by specifically binding to the HIV-1 RNA, anchoring it to the cell membrane for budding or viral particles (Meric, et al., *J. Virol.* 63: 1558–1658 (1989) Gorelick, et al., *Proc. Natl. Acad. Sci. USA* 85: 8420–8424 (1988), Aldovini, et al., *J. Virol.* 64: 1920–1926 (1990), Lever, et al., *J. Virol.* 63: 4085–4087 (1989)). Site-directed mutagenesis studies demonstrated that modification of Cys or His residues results in defective viral RNA packaging and noninfectious viral particles are formed (Aldovini, et al., *J. Virol.* 64: 1920–1926 (1990), Lever, et al., *J. Virol.* 63: 4085–4087 (1989)). The highly abundant nonhistone nuclear protein of eukaryotes, poly (ADP-ribose) polymerase (E.C.2.4.4.30), also contains two CCHC-type zinc fingers located in the basic terminal polypeptide domain, as analyzed by site directed mutagenesis (Gradwohl, et al., *Proc, Natl. Sci. USA* 87: 2990–2992 (1990)).

Published experiments have shown that aromatic C-nitroso ligands of poly (ADP-ribose) polymerase preferentially destabilize one of the two zinc fingers coincidental with a loss of enzymatic activity but not DNA binding capacity of the enzyme protein (Buki, et al., *FEBS Lett.* 290: 181–185 (1991)). Based on the similarity to results obtained by site-directed mutagenesis (Gradwohl, et al., *Proc. Natl. Acad. Sci. USA* 87: 2990–2992 (1990)), it appears that the primary attack of C-nitroso ligands occurred at zinc finger FI (Buki, et al., *FEBS Lett.* 290: 181–185 (1991)). A selective cytocidal action of the C-nitroso group containing poly (ADP-ribose) polymerase ligands on cancer cells was subsequently discovered (Rice et al., *Proc. Natl. Acad. Sci. USA* 89: 7703–7707.

Based on the coincidental occurrence of the CCHC type zinc fingers in both retroviral NC proteins and in poly (ADP-ribose) polymerase and the observed chemotherapeutic effects of C-nitroso-containing ligands on cancer cells, experiments were initiated to test if the C-nitroso compounds also have antiviral effects on retroviruses containing NC proteins. As described herein experiments testing this hypothesis with the polypeptide corresponding to the N-terminal CCHC zinc finger of HIV-1 NC protein, Zn (HIV1-F1) (South, et al., *Am. Chem. Soc.* 111: 395–396 (1989), South, et al., *Biochem. Pharm.* 40: 123–129 (1990), Summers, et al., *Biochemistry* 29: 329–340 (1990)), intact HIV-1 virions and on the propagation of HIV-1 in human lymphocytes in culture, were performed.

SUMMARY OF THE INVENTION

The subject invention provides for novel anti-tumor compounds, anti-retroviral compounds and retroviral inactivating compounds. These compounds include 6-nitroso-1, 2-benzopyrone, 3-nitrosobenzamide, 2-nitrosobenzamide, 4-nitrosobenzamide, 5-nitroso-1(2H)-isoquinolinone, 7-nitroso-1(2H)-isoquinolinone, 8-nitroso-1(2H)-isoquinolinone.

The invention also provides for compositions containing one or more of the compounds, and for methods of treating retroviral infections and cancer with these compounds and compositions.

Also provided for are methods of treating cancer and retroviral infections with 2-nitrosobenzamide, 3-nitrosobenzamide and 4-nitrosobenzamide. Compositions containing one or more of these compounds are also provided.

Another aspect of the invention is to provide methods for inactivating viruses, especially retroviruses, in biological materials, e.g., blood, by adding various nitroso compounds including 6-nitroso-1,2-benzopyrone, 2-nitrosobenzamide, 3-nitrosobenzamide, 4-nitrosobenzamide, 5-nitroso-1(2H)-isoquinoline, 7-nitroso-1(2H)-isoquinoline and 8-nitroso-1(2H)-isoquinoline.

Another aspect of the invention is to provide methods for inactivating AZT resistant viruses, in particular HIV and SIV by adding various nitroso compounds including 6-nitroso-1,2-benzopyrone, 2-nitrosobenzamide, 3-nitrosobenzamide, 4-nitrosobenzamide, 5-nitroso-1(2H)-isoquinoline, 7-nitroso-1(2H)-isoquinoline and 8-nitroso-1(2H)-isoquinoline.

Another aspect of the invention is to provide methods for reducing the level of integrated viral DNA from the genome of a host, in particular integrated HIV DNA in a mammalian host, by adding various nitroso compounds including 6-nitroso-1,2-benzopyrone, 2-nitrosobenzamide, 3-nitrosobenzamide, 4-nitrosobenzamide, 5-nitroso-1(2H)-isoquinoline, 7-nitroso-1(2H)-isoquinoline and 8-nitroso-1(2H)-isoquinoline.

An additional aspect of the subject invention is to provide novel compositions of biological materials comprising biological material and the compounds used in the subject methods.

DESCRIPTION OF THE FIGURES

FIG. 4 is a graph showing that NOBP and NOBA inhibit the ability of human leukemic cells (855-2 and HL-60) to form colonies (CFU) from single cells in a semi-solid medium.

FIGS. 6A–6D show graphs displaying the inhibitory effects of NOBP, NOBA and NOQ on four human brain tumor cell lines.

FIG. 7 is a graph comparing the effectiveness of NOBP with vincristine.

FIG. 13 B. shows an HIV-1 inactivation assay using NOBA at different temperatures. The assay was performed as described in FIG. 13A except that the 30 min. preincubation of virus with NOBA was carried out at 0°, 22° or 37° C.

FIG. 13 C. shows the dose-responsive effect of NOBA on PHA-PBL viability. PHA-PBL ($10^6$/ml) were treated with increasing doses of NOBA for 24 hours in the presence of MTT substrate and the relative absorbance at 550 nm reflects the metabolic activity of the cells. The level of product formation in the absence of NOBA was considered to be 100% and all experimental values were normalized to that control value.

In FIG. 14A, ordinate=p27 antigen assay (ELISA) performed on day 10; abscissa= concentration of NOBA or DMSO. In FIG. 14B, cell viability test determined on day 10 by the tetrazolium assay first line bars=virus infected cells (SIV) in presence of NOBA; second line bars (controls)=uninfected cells treated with NOBA.

FIG. 15A shows the amplification of SIV p27 core antigen protein with gag-selective primers. FIG. 15B shows the amplification of ubiquitous B-actin gene.

(FIG. 16A) Virus titers in the supernatant of cultures 16 days from initial co-cultivation as determined by the SIV p27 core antigen capture ELISA. (FIG. 16BB) Viability of cell cultures 16 days from initial co-cultivation as determined by the MTT assay. Data presented are the average of duplicate wells.

DESCRIPTION OF SPECIFIC EMBODIMENTS

Definitions

Figure 1:
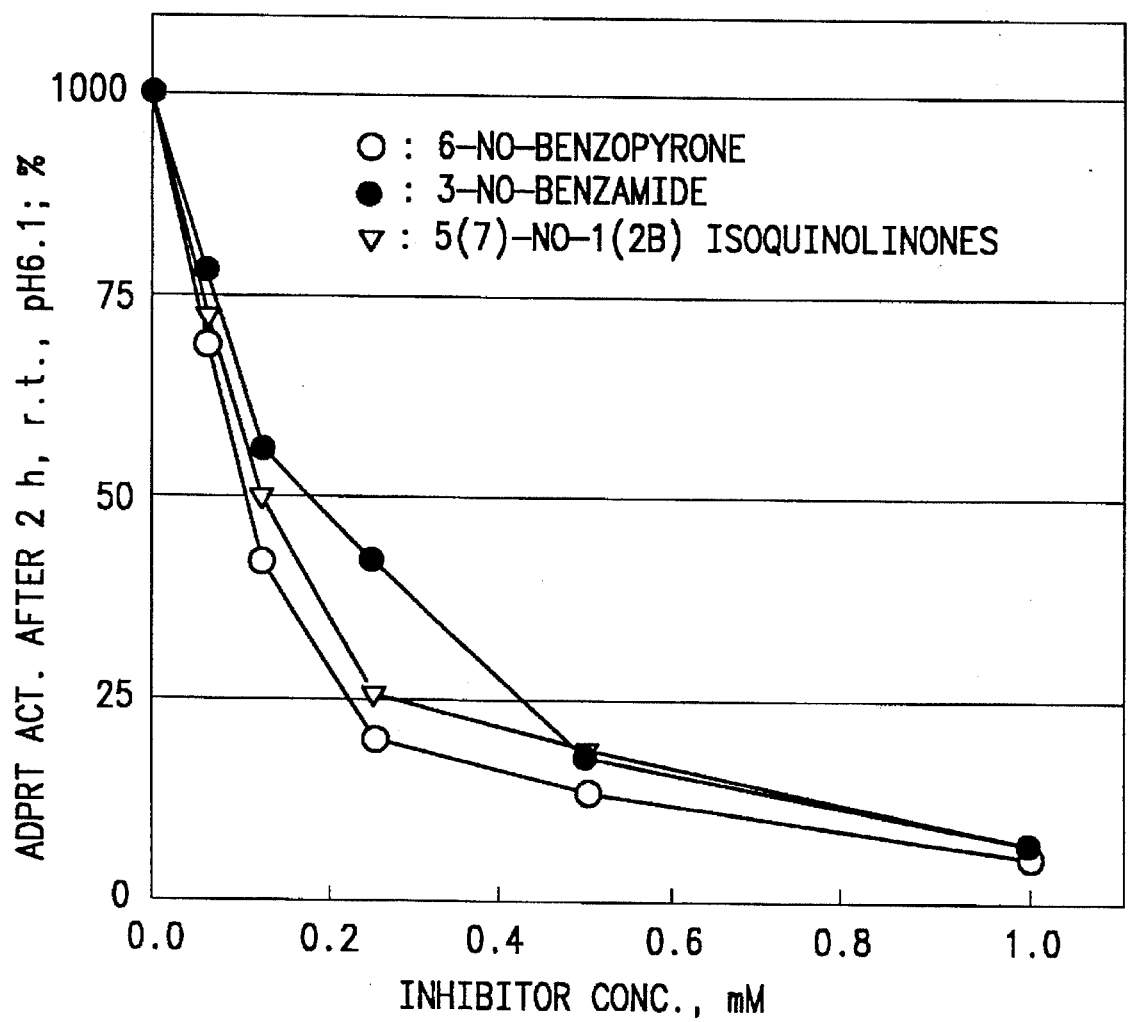
FIG. 1 is a graph comparing the degree of ADRPT polymerase activity (ADPRP) inactivation exhibited by different concentrations of 6-nitroso-1,2-benzopyrone, 3-nitroso-benzamide, and nitroso-1(2H)-isoquinolinones (NOQ) (a mixture of the 5 and 7 nitroso isomers).
Figure 2A:
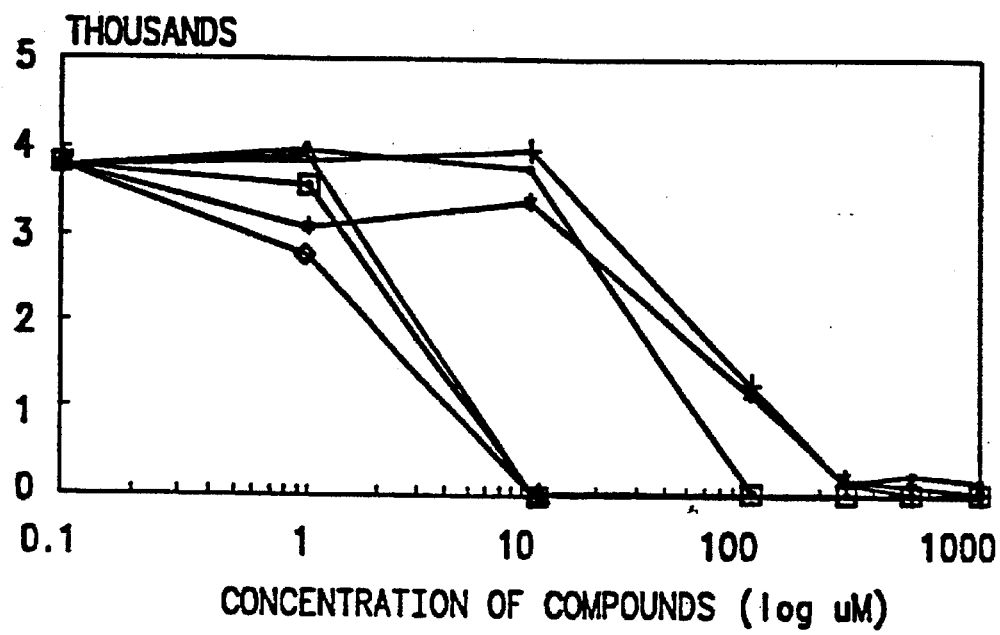
FIGS. 2A–2F are a composite of graphs displaying the inhibitory effects of the ADRPT ligands on (FIG. 2A) 855-2 cells (a cell line of human B-cell lineage acute lymphoblastic leukemia), (FIG. 2B) H9 cells (a cell line of human T-cell lineage acute lymphoblastic leukemia), (FIG. 2C) HL-60 cells (a cell line of human acute nonlymphoblastic leukemia) and (FIG. 2D) K562 cells (a cell line of human chronic myelogenous leukemia). These cells were cultured while under the influence of the growth factors in 10% fetal bovine serum (FCS), whereas in (FIG. 2E) and (FIG. 2F) the 855-2 cells were cultured in the presence of autocrine growth factor activity (AGF) or low molecular weight-B-cell growth factor (BCGF, a T-cell derived lymphokine), respectively.
Figure 2B:
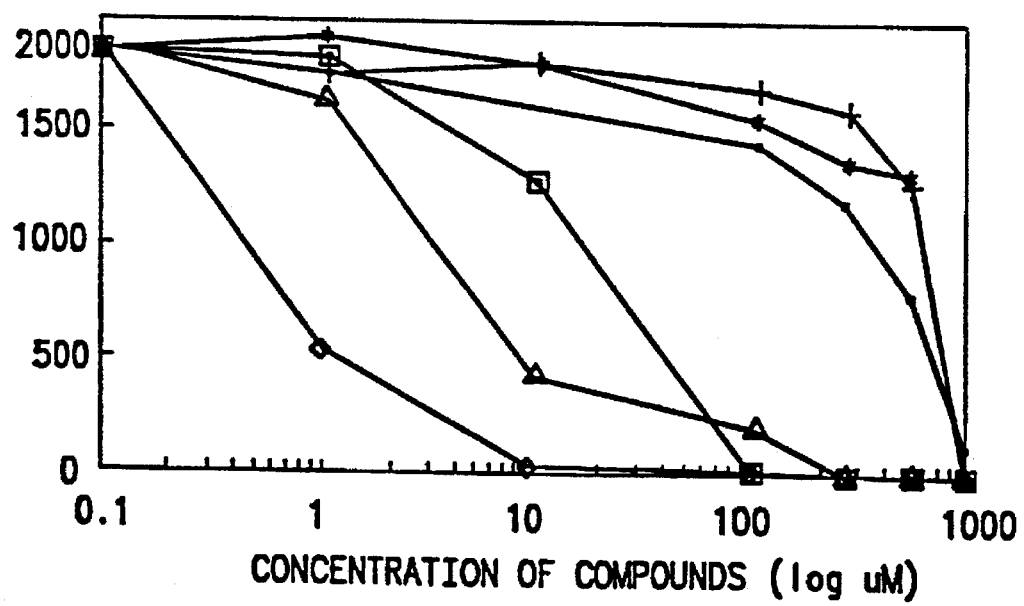
Figure 2C:
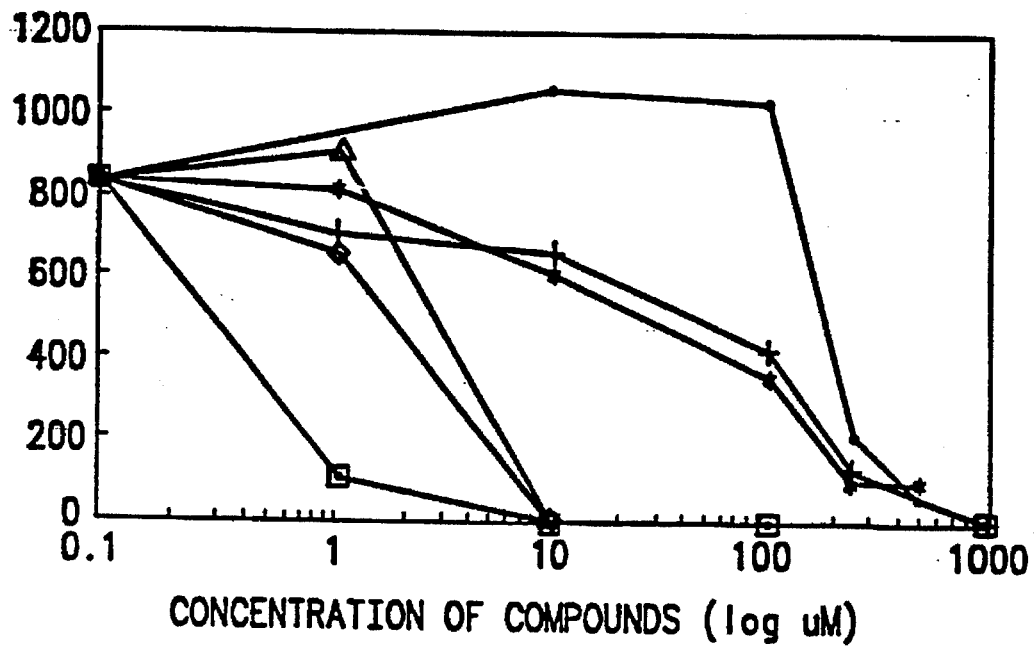
Figure 2D:
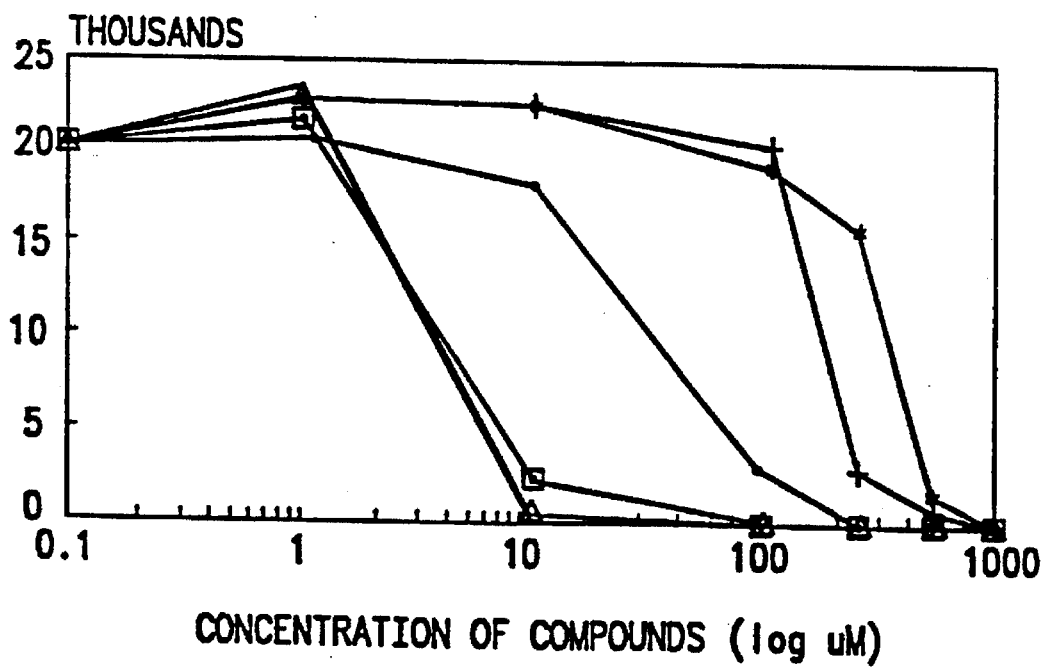
Figure 2E:
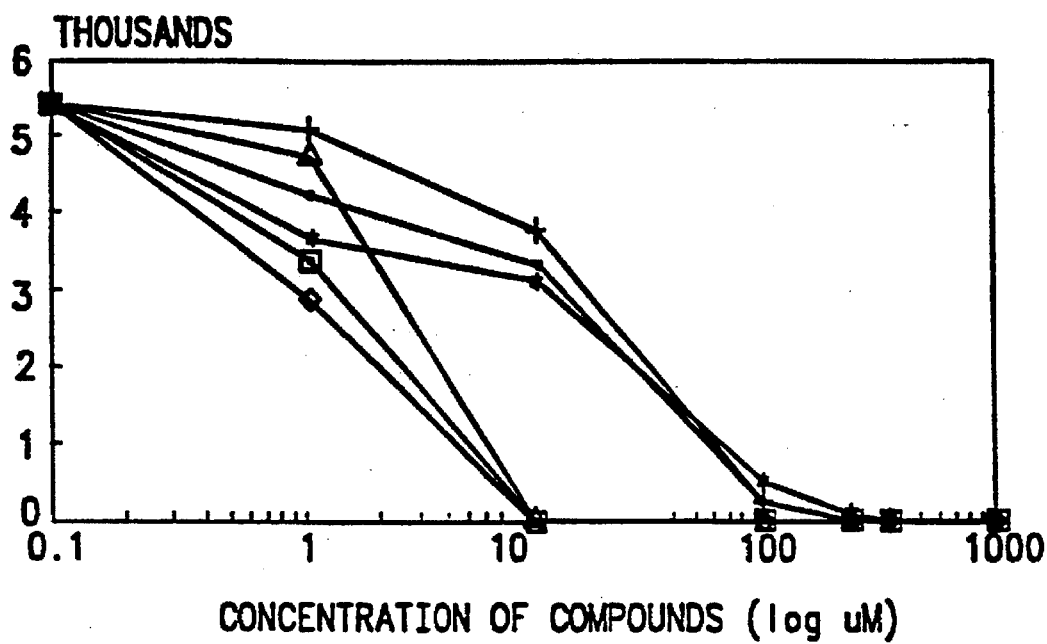
Figure 2F:
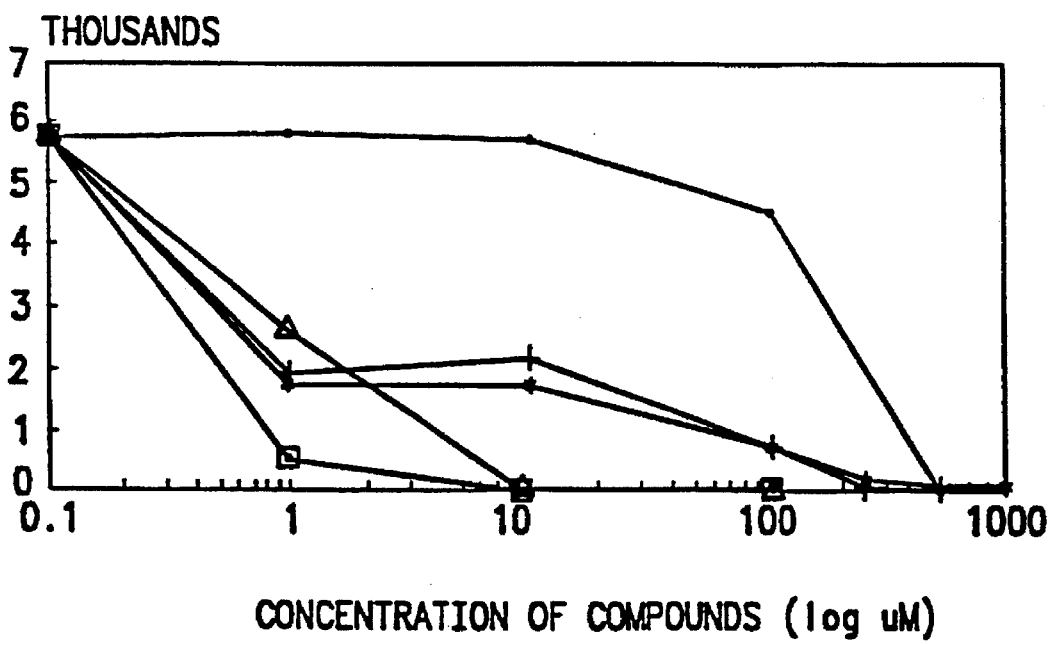

The term "biological material" as used herein, refers to any biological material extracted from a living organism, including blood, plasma, cerebrospinal fluid, organs, and the like, as well as the processed products of biological material extracted from a living organism.

The term "biological composition" as used herein, refers to a composition comprising a biological material and a compound of interest.

The term "cancer" as used herein, refers to malignant tumors consisting of cells that do not follow normal control signals for proliferation or positioning.

The term "retrovirus" as used herein refers to RNA viruses which utilize the enzyme reverse transcriptase to transcribe infecting RNA chains into DNA complements.

The term "zinc finger" refers to a structural domain of a protein capable of binding a zinc atom. The nature of zinc finger proteins domains is well described in the literature, e.g., Klug and Rhodes, *Trends in Biochemical Sciences* 12: 464–469 (1987).

The Invention

The subject invention provides for several nitroso compounds that are ADPRT polymerase activity inhibitors. These compounds find use as anti-tumor and anti-viral compounds.

Compound (I) has the following formula:

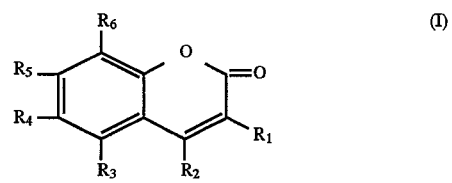

wherein $R_1$, $R_2$, $R_3$, $R_4$, $R_5$, and $R_6$ are selected from the group consisting of hydrogen and nitroso, and only one of $R_1$, $R_2$, $R_3$, $R_4$, $R_5$, and $R_6$ is a nitroso group.

A preferred embodiment of compound I is where $R_4$ is the nitroso group, i.e., the molecule 6-nitroso-1,2-benzopyrone.

Compound II has the formula:

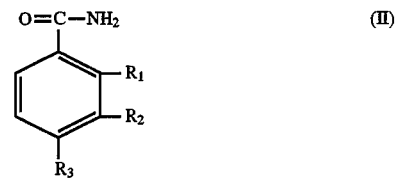

wherein $R_1$, $R_2$, and $R_3$ are selected from the group consisting of hydrogen and nitroso, and only one of $R_1$, $R_2$, and $R_3$ is a nitroso group.

Compound III has the formula:

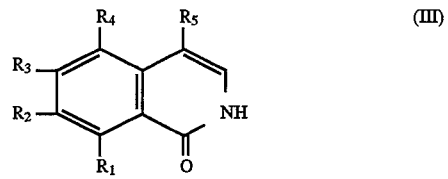

wherein $R_1$, $R_2$, $R_3$, $R_4$, and $R_5$ are selected from the group consisting of hydrogen and nitroso, and only one of $R_1$, $R_2$, $R_3$, $R_4$, and $R_5$ is a nitroso group.

Preferred embodiments of compound III are where either $R_2$ or $R_4$ is the nitroso group, i.e., 7-nitroso-1(2H)-isoquinolinone and 5-nitroso-1(2H)-isoquinolinone, respectively.

The disclosed synthesis for 5-nitroso-1(2H)-isoquinolinone may produce 2 closely related structural isomers, 7-nitroso-1(2H)-isoquinolinone and 8-nitroso-1(2H)-isoquinolinone. Although experiments testing the biological activity of 5-nitroso-1(2H)-isoquinolinone may have contained significant quantities of 8-nitroso-1(2H)-isoquinolinone or 7-nitroso-1(2H)-isoquinolinone, all three isomers are believed to possess similar anti-tumor and anti-viral activity on the basis of their close structural similarity. This hypothesis may be conveniently tested by separating the isomers by thin layer chromatography or similar methods, and comparing the anti-tumor and anti-viral activities of the separated compounds.

Detailed synthesis of 6-nitroso-1,2-benzopyrone, 3-nitroso-benzamide, 5-nitroso-1(2H)-isoquinolinone, 7-nitroso-1(2H)-isoquinolinone, and 8-nitroso-1(2H)-isoquinolinone, is provided in the example section below.

In general, the nitroso compounds of the subject of invention may be synthesized by oxidizing a corresponding amino compound to a compound of the subject invention by oxidation with 3-chloroperoxybenzoic acid (or other peroxyacids) in ethyl acetate, a halocarbon solvent or in a relatively concentrated solution in dimethyl formamide.

Detailed synthesis of 3-nitrosobenzamide is described in the example section below. Synthesis of the other precursor amino compounds are described in the chemical literature.

Some of the compounds are commercially available. Some precursor amino compounds for oxidation to nitroso compounds of the subject invention are as follows: 3-amino-1,2-benzopyrone (Spectrum Chemical Mfg. Corp., Gardena, Calif. 90248); 4-amino-1,2-benzopyrone (Aldrich, Rare Chemical Catalog); 5-amino-1,2-benzopyrone (by reduction of 5-nitro-1,2-benzopyrone, *Chem. Abst.* 57 16536d (1962)); 7-amino-1,2-benzopyrone (Gottlieb, et al., *J. Chem. Soc. Perkin. Trans. II* 435 (1979)); 8-amino-1,2-benzopyrone (by reduction of 8-amino-1,2-benzopyrone, Abdel-Megid, et al., *Egypt J. Chem.* 20: 453–462 (1977)), and 4-amino-1(2H)-isoquinolinone, by reduction of the corresponding 4-nitro analog (Horning, et al., (1971) *Can. J. Chem.* 49: 2785–2796).

In addition to compounds (I) to (III), the subject invention contemplates various structurally related compounds that have similar carcinostatic and/or anti-viral activities. These structurally related compounds could be conveniently screened on the basis of their highly potent inhibitory effect on ADPRT polymerase activity. Structurally related compounds of interest include derivatives substituted by additional nitroso groups and small, e.g., $C_1$–$C_3$ alkyl groups. Also of interest are various nitroso substituted structurally related heterocyclic rings such as 3,4-dihydro-1(2H)-isoquinolinones, nicotinamides, pthalhydrazides, and 1,3-benzoxazine-2,4-diones.

Another aspect of the compounds of the subject invention are the ease with which they permeate cell membranes and their relative absence of non-specific binding to proteins and nucleic acid.

In practice, the ADPRT polymerase inhibitors of this invention, namely compounds (I) to (III), and any of their pharmaceutically acceptable salts, may be administered in amounts, either alone or in combination with each other, and in the pharmaceutical form which will be sufficient and effective to inhibit neoplastic growth or viral replication or prevent the development of the cancerous growth or viral infection in the mammalian host.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is intravenous, except in those cases where the subject has topical tumors or lesions, where the topical administration may be proper. In other instances, it may be necessary to administer the composition in other parenteral or even oral forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an effective amount of at least one of compounds (I) to (III), or pharmaceutically acceptable salts thereof, and in addition it may include any conventional pharmaceutical excipients and other medicinal or pharmaceutical drugs or agents, carriers, adjuvants, diluents, etc., as customary in the pharmaceutical sciences.

For solid compositions, in addition to the compounds (I) to (III), such excipients as, for example, pharmaceutical grades of mannitol, lactose, starch, magnesium stearate, sodium saccharin, talcum, cellulose, glucose, sucrose, magnesium carbonate, and the like may be used. The compounds of the subject invention may be also formulated as suppositories using, for example, polyalkylene glycols, for example, propylene glycol, as the carrier.

Liquid, particularly injectable compositions can, for example, be prepared by dissolving, dispersing, etc., at least one of active compounds (I) to (III) in a pharmaceutical solution such as, for example, water, saline, aqueous dextrose, glycerol, ethanol, DMSO and the like, to thereby form the injectable solution or suspension.

If desired, the pharmaceutical composition to be administered may also contain minor amounts of nontoxic auxiliary substances such as wetting or emulsifying agents, pH buffering agents, and other substances such as, for example, sodium acetate, triethanolamine oleate, etc.

If desired, the pharmaceutical composition to be administered may contain liposomal formulations comprising a phospholipid, a negatively charged phospholipid and a compound selected from chloresterol, a fatty acid ester of chloresterol or an unsaturated fatty acid. Compounds I, II or III may be encapsulated or partitioned in a bilayer of liposomes of the liposomal formulation according to U.S. patent application Ser. No. 08/020,035 entitled "Liposomal Formulations and Methods of Making and Using Same" filed on Feb. 19, 1993 which is incorporated herein by reference.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

A more recently devised approach for parenteral administration employs the implantation of a slow-release or sustained-release systems, which assures that a constant level of dosage is maintained, according to U.S. Pat. No. 3,710,795, which is incorporated herein by reference.

Any of the above pharmaceutical compositions may contain 0.01–99%, preferably 1–70% of the active ingredient.

Actual methods of preparing such dosage forms are known, or will be apparent to those skilled in this art, and are described in detail in *Remington's Pharmaceutical Sciences*, Mack Publishing Company, Easton, Pa., 17th Edition, 1985. The composition or formulation to be administered will, in any event, contain such quantity of the active compound(s) that will assure that a therapeutically effective amount will be delivered to a patient. A therapeutically effective amount means an amount effective to prevent development of or to alleviate the existing symptoms of the subject being treated.

The amount of active compound administered will, of course, be dependent on the subject being treated, on the subject's weight, the severity of the affliction, the manner of administration and the judgment of the prescribing physician. However, an effective dosage may be in the range of 1 to 12 mg/kg/day, preferably 1 to 5 mg/kg/day, given only for 1–2 days at one treatment cycle. Generally, the upper limit for the drug dose determination is its efficacy balanced with its possible toxicity.

The subject invention provides for methods of reducing the titer of infectious retroviruses, particularly retroviruses (including the retrovirus HIV-1) in biological materials by inactivating the viruses. Viruses may be inactivated by contact between the compound of interest and the virus. The term "reducing" includes the complete elimination of all the infectious viruses of interest, as well as a diminution in the titer of the infectious viruses. It is of particular interest to reduce the number of infectious viruses in biological material that is to be introduced into a living organism so as to reduce the possibility for infection. It is also of interest to reduce the titer infectious viruses that might be present in or on non-biological materials that come into contact with living organisms, such non-biological materials include surgical instruments, dental instruments, hypodermic needles, public sanitary facilities, and the like.

A preferred embodiment of the subject invention is the reduction in infectious virus concentration in blood.

Another preferred embodiment of the subject invention is the inactivation of AZT resistant viruses and retroviruses.

Yet another aspect of the subject invention is the removal of integrated retroviral DNA from the genome of a host.

Although the effective amount of the viral-inactivating compound used in the subject method will vary in accordance with the nature of the compound and the particular material, biological or otherwise of interest, a preferred concentration of 3-nitrosobenzamide is about 15 micromolar. An effective amount may readily be determined by testing the effect of a range of concentrations of the compound of interest on the viral titer of a composition containing a virus of interest.

The subject methods of reducing infectious virus concentration in biological materials inactivate viruses by employing the step of adding an effective amount of compounds I, II or III, or combinations thereof. These nitroso compounds can destabilize $Zn^{+2}$ fingers, i.e. eject $Zn^{+2}$ of the nucleocapsid proteins of viruses, particularly retroviruses. Preferred embodiments of compounds I, II and III for use in inactivating viruses are 6-nitroso-1,2-benzopyrone, 3-nitrosobenzamide, 5-nitroso-1(2H)-isoquinoline, 7-nitroso-1(2H)-isoquinoline, 8-nitroso-1(2H)-isoquinoline, and 3-nitrosobenzamide. The use of 3-nitroso benzamide is particularly preferred.

Another aspect of the invention is to provide for novel compositions consisting of biological materials containing an effective amount of nitroso compounds I, II and III, or combinations thereof. Preferred embodiments of compounds I, II and III for use in the subject composition are 6-nitroso-1,2-benzopyrone, 3-nitrosobenzamide, 5-nitroso-1 (2H)-isoquinoline, 7-nitroso-1(2H)-isoquinoline, 8-nitroso-1(2H)-isoquinoline, 2-nitrosobenzamide, 4-nitrosobenzamide, and 3-nitrosobenzamide. The use of 3-nitrosobenzamide is particularly preferred. The subject biological compositions may have diminished viral concentrations and may thus be administered with less risk of infection than comparable biological materials.

The subject invention also provides for methods of detecting compounds that can inactivate viruses, particular retroviruses, by testing for the effect of $Zn^{+2}$ finger destabilizing, i.e. $Zn^{+2}$ ejecting, compounds on the titer of a virus. Virus titer may be measured by well known methods suitable for measuring the titer of a virus of interest. The ejection of $Zn^{+2}$ from a zinc finger domain may be measured, among other methods, by NMR and/or $^{65}Zn^{+2}$ as described herein and as described in Buki, et al., *FEBS. Lett.*, 290: 181–185 (1991).

The invention having been described, the following examples are offered to illustrate the subject invention by way of illustration, not by way of limitation.

EXAMPLES

I. Synthesis and Characterization of 6-Nitroso-1,2-Benzopyrone

An example of a method for the preparation of 6-nitroso-1,2-benzopyrones is provided as follows:

To a stirred solution of 6-amino-1,2-benzopyrone hydrochloride (4.00 g, 20 mmol) in water (40 ml) at 22° C. was added a solution of sodium tungstate (5.93 g, 20 mmol) in water (20 ml) followed by 30% aqueous hydrogen peroxide (5 ml) and stirring was continued for 1.5 hours. The oxidation product was extracted from the green-colored mixture with two 100 ml volumes of ethyl acetate, the combined extracts washed with 0.1N HCl (50 ml) and then water (100 ml). The ethyl acetate was removed by rotary evaporation and the residue recrystallized from warm ethanol (250 ml).

Analysis of Reaction Product

The green crystals obtained from the recrystallization step (1.48 g, 42% yield) displayed light absorption at 750 nm characteristic of monomeric arylnitroso compounds. Mass spectrum: m/z (relative intensity): 175 ($M^+$, 100), 161 (16.88), 145 (33.77), 133 (10.38), 117 (56.09), 89 (79.71), 63 (57.13). High resolution data for the $M^+$ peak: calculated for $C_9H_5NO_3$: 175.0268; found: 175.0271 (deviation–1.1 ppm). $^1$H-NMR (CDCl$_3$, 300 MHz) $\delta$ (ppm) from TMS: doublet (6.572 and 6.604) H-4 split by H-3; doublet (7.472 and 7.501) H-8 split by H-7; doublet of doublets (7.860/ 7.866 and 7.889/7.798) H-7 split by H-8 and finely split by H-5; doublet (7.910 and 7.942) H-3 split by H-4; doublet (8.308 and 8.315) H-5 finely split by H-7. UV/VIS spectrum in ethanol, $\lambda$ max ($\epsilon$): 750 nm (46), 316 nm (8.96×10$^3$), 274 nm (2.24×10$^4$) Melting Point: The compound polymerizes above 160° C., blackens and melts in the range of 325°–340° C.

This nitroso-compound may also be prepared by reacting 6-amino-1,2-benzopyrone (as the free base) with 3-chloroperoxybenzoic acid in ethyl acetate or halocarbon solvents.

II. Synthesis of 3-nitrosobenzamide

To a stirred solution of 3-aminobenzamide (Aldrich Chemical Co.) (0.476 g, 3.50 mmol) in ethyl acetate (50 ml) at ambient temperature was added 1.208 g of 3-chloroperoxybenzoic acid (commercial grade, 50–60% purity, Aldrich), whereupon the solution turned green. After 10 minutes the mixture was extracted with 0.14M aqueous sodium bicarbonate (58 ml), washed with three successive 40-ml portions of water, dried over sodium sulfate, then reduced in volume to 20 mL by rotary evaporation and placed in the freezer (–20° C.), whereupon the product slowly deposited as a light yellow solid during a period of 72 hours (0.180 g, 34% yield).

The 2-nitrosobenzamide and 4-nitrosobenzamide isomers may be similarly prepared by oxididizing 2-aminobenzamide and 4-aminobenzamide, respectively.

Analysis of Reaction Product

Melting point: The substance darkens above 135° C., softens and apparently polymerizes in the range 150°–160° C., and melts at 240°–250° C. (with decomposition). In solution the compound is green-blue. Mass spectrum: m/z (relative intensity): 150 ($M^+$, 100), 136 (10.9), 120 (77.2), 103 (31.6), 92 (46.5), 85 (22.8), 71 (33.3). High resolution data for the $M^+$ peak: calculated for $C_7H_6N_2O_2$: 150.042928; found: 150.042900 (deviation–0.2 ppm). NMR spectrum: $^1$H-NMR (DMSO-d$_6$, 300 MHz) $\delta$ (ppm) from TMS: broad singlet (7.737) N—H; t (7.824, 7.850, 7.875) H-5 split by H-4 and H-6; d (8.059 and 8.086) H-6 split by H-5; d (8.357 and 8.383) H-4 split by H-5; s (8.472) H-2. The singlet at 7.737 corresponds to 1 proton; the second N—H proton, spectrally non-equivalent in this compound, is overlaid by the doublet of H-4. This doublet integrates to 2 protons and can be resolved by addition of D$_2$O to the DMSO solution. UV-VIS absorption spectrum in absolute ethanol, $\lambda$max ($\epsilon$): 750 nm (37.6), 304 nm (5.35×10$^3$) and 218 nm (1.50×10$^4$). An absorption maximum at 750 nm is characteristic of monomeric arylnitroso compounds.

In another embodiment, 3-nitrosobenzamide is synthesized by dissolving 3-aminobenzamide (5.0 g) in N,N-dimethylformamide (DMF) solvent (25 ml) and then chilled in an ice bath. 3-Chloroperoxybenzoic acid (2.1 equivalents)

is also dissolved in DMF solvent (25 ml) in a 250-ml flask equipped with a stirrer and thermometer and, as needed, an ice bath. This solution is chilled to 0°–5° C., the ice bath is removed, and to it, with stirring, is added all at once the chilled 3-aminobenzamide solution. The mixture immediately becomes a transparent brown color, but within 0.5 minute turns to a deep green, and within 1.0 minute the temperature rises to 70° C., at which time the ice bath is reapplied to the reaction flask whereupon the temperature begins to fall, and is allowed to fall to 25° C., and stirring is continued for a total of 5 minutes. Some precipitation occurs (3,3'-azoxybenzamide side-product), thereafter the mixture is chilled to 5° C. for 10 minutes. The chilled mixture is filtered (suction) to remove the azoxy precipitate, and the green filtrate is poured into chilled (5°–10° C.) and stirred aqueous 0.40M $Na_2CO_3$ (200 ml), resulting in a light green suspension, and the suspension is stirred for an additional 10 minutes at 5°–10° C. to assure maximal product precipitation. Note that the pH of the suspension is about 8.5, which assures that 3-chlorobenzoic acid is retained in the aqueous solution as the sodium salt. The precipitate is then collected on a suction funnel and rinsed with deionized water (100 ml). This material, which is 3-NOBA (mostly as the tan dimer) containing residual 3,3'-azoxybenzamide side-product impurity, is then transferred, while damp, to a suitable flask and to it is added 50% aqueous acetic acid (200 ml). The mixture is warmed to 65°–70° C. to dissolve the dimer into the soluble monomeric 3-NOBA (green) and stirred for 5 minutes at 65° C. The azoxy impurity (yellow) is poorly soluble and remains undissolved. The warm mixture is filtered (gravity) to give a clear green filtrate, which is allowed to cool. It is then chilled and placed in the refrigerator freezer (–20° C.) overnight to allow the 3-NOBA to redeposit as the light tan solid dimer. On the following day the solid product is collected on a suction filter, rinsed with fresh solvent, and the product cake is then dried by vacuum under mild warming for several hours. One typically obtains 2.24 g of dry 3-NOBA containing a trace of the azoxy impurity. The product is recrystallized by dissolving it again in 50% aqueous acetic acid (120 ml) and allowing to redeposit overnight in the freezer. After collection, rinsing and drying in vacuo, the weight is 2.08 g. (37% overall yield). TLC shows the material is 3-NOBA with a trace of the azoxy impurity.

III. Synthesis of Nitroso-1(2M) -isoquinolinones (a mixture of 5-nitroso and 7-nitroso-isomers)

1(2H)-Isoquinolinone (isocarbostyril) (Aldrich) was nitrated using a general method for isoquinoline compounds (C. G. LeFevre and R. J. W. LeFevre, *J. Chem. Soc.* 1470 (1935)). The nitration product (a mixture of the 5-nitro and 7-nitro isomers, as assigned by Y. Kawazoe and Y. Yoshioka, *Chem. Pharm. Bull.* (Tokyo) 16: 715–720 (1968), although one of the isomers could be the 8-nitro isomer) was then reduced to the corresponding amino-1(2H)-isoquinolinones using a combination of potassium borohydride and palladium-on-carbon catalyst in aqueous methanol. To the resultant amino-1(2H)-isoquinolinones (as free bases) (0.560 g, 3.50 mmol) in ethyl acetate (175 mL) at 30° C. was added 1.208 g of 3-chloroperoxybenzoic acid (Aldrich). The mixture became cloudy and after 20 minutes it was filtered, extracted with 0.14M sodium bicarbonate (58 mL), washed with two 50-mL portions of water, and dried over sodium sulfate. The volume of the solution was reduced to 50 mL by rotary evaporation and then placed in the freezer (–20° C.), whereupon an orange solid product was deposited (0.102 g).

Analysis of Reaction Product

Melting point: substance darkens above 175° C., softens, blackens and apparently polymerizes above 195° C., and finally melts in the range 310°–335° C. NMR analysis: $^1$H-NMR (DMSO-$d_6$/$D_2O$, 300 MHz) δ (ppm) from TMS: m (6.723, 6.741, 6.752); m (7.511, 7.518, 7.533, 7.539, 7.547, 7.559, 7.577, 7.585); m (7.663, 7.674, 7.686. 7.698, 7.707); d (7.818, 7.846). In the absence of $D_2O$, the compound also displays a broad singlet at 11.90 ppm. The isomeric components were analytically resolved by thin-layer chromatography (silica gel plates, ethyl acetate solvent), giving two bands, $R_f$ 0.82 and $R_f$ 0.72. Mass spectrum for $R_f$ 0.82: m/z (relative intensity): 174 ($M^+$, 100), 160 (26.8), 144 (93.0), 117 (90.8), 97 (21.9), 89 (96.1), 71 (24.1). High resolution data for the $M^+$ peak: calculated for $C_9H_6N_2O_2$: 174.042928; found: 174.043200 (deviation=–0.3 ppm). For the component having $R_f$ 0.72, $M^+$, calculated for $C_9H_6N_2O_2$: 174.042928; Found: 174.043200 (deviation=–1.6 ppm). These data confirm that the compounds are mono-nitroso isomers.

IV. ADPRT Inactivation Studies

The compounds of the subject invention were tested for their ability to inactivate the polymerase activity of adenosinediphosphoribosyl transferase (ADPRT). Assays were performed according to the method of Buki and Kun, *Biochem.* 27: 5990–5995 (1988), using calf thymus ADPRT. The assay results as given in Table I provide the $I_{50}$ (the concentration of the compound that inhibits enzyme activity 50%) values for ADPRT of the nitroso precursor (6-amino-1,2-benzopyrone) and the more potent 5-iodo-derivative (Table I, compounds 1 and 2, respectively). The nitroso compounds (3,4,5 in Table I) are all highly active as anti-tumor and anti-HIV molecules (as shown in later sections) and are effective even after exposure of cells for a period as short as 30 minutes. 5-I-6-nitroso-1,2-benzopyrone (compound 6) in these studies has been shown to be a relatively poor inhibitor of ADRPT (it is believed that the iodo substitution deactivates the NO group as an electrophile) and its biological action is 10 times weaker than that of 6-NO-1,2-benzopyrone. For these reasons, the compositions of the present invention are believed to be superior to 5-I-6-nitroso-1,2 benzopyrone, which has been shown to be a poor permeant molecule.

TABLE I $I_{50}$ data for aromatic inhibitors of ADPRT

| No. | Inhibitor | $I_{50}$, μM |
|-----|-----------|--------------|
| 1 | 6-$NH_2$-1,2-benzopyrone* | 370 |
| 2 | 5-I-6-$NH_2$-1,2-benzopyrone* | 41 |
| 3 | 3-NO-benzamide | 15 |
| 4 | 5(7)-nitroso-(2H)-isoquinolinone** | 13 |
| 5 | 6-NO-1,2-benzopyrone | 40 |
| 6 | 5-I-6-NO-1,2-benzopyrone | 400 |

*biochemical precursor of nitroso compounds 5 and 6
**a mixture of the 5- and 7-nitroso compounds
Assay conditions: ADPRT, 0.4 μg; coDNA, 4 μg; inhibitor diluted between 0.8 and 600 μM, in 50 μl of 50 mM Tris-HCl, 50 mM KCl, 5 mM 2-mercaptoethanol, 0.5 mM EDTA, 0.1 mM NAD ([32-P]-labelled), pH 7.5. Polymerization at 25° C. for 4 minutes.

FIG. 1 illustrates the % inactivation of ADPRT polymerase activity observed after 2 hours of incubation with the nitroso-compound inhibitors at several concentrations.

Additional experiments involving the equilibration between $^{65}Zn^{+2}$ and ADPRT-bound $Zn^{+2}$ suggest that the ADPRT inhibition activity of the nitroso compounds appears to act by destabilizing the protein through the ejecting of $Zn^{+2}$. (Buki K. G., Bauer P. T., Mendeleyev, F.; Hakam, H. and Kun E. (1991) *FEBS Lett.* 290: 181–185). The above mechanism of action for ADPRT inhibitors is speculative and does not constitute any limitation on claimed subject matter.

V. Biological Anti-Cancer Activities of Nitrosobenzopyrones, Nitrosobenzamides and Nitroso-isoquinolinones Experiments were performed in which various human leukemia cell lines were exposed to increasing concentrations of 6-amino-1,2-benzopyrone (ABP), 5-iodo-6-amino-1,2-benzopyrone (IABP), 6-nitro-1,2-benzopyrone ($NO_2BP$), 6-nitroso-1,2-benzopyrone (NOBP), 3-nitrosobenzamide (NOBA) or 5(7)-nitroso-1(2H)-isoquinolinone (NOQ) (a mixture of the 5-nitroso and 7-nitroso isomers), and the level of [$^3H$] thymidine uptake was determined as a measure of cellular proliferation. As shown in FIG. 2, for each of the cell lines tested (855-2 cells, FIG. 2A; H9 cells, FIG. 2B; HL-60 cells, FIG. 2C; K562 cells, FIG. 2D) the nitroso-containing ligands (NOBP, NOBA, NOQ) were able to inhibit $^3$H-thymidine uptake in lower molar concentrations than the other compounds. NOBP, NOBA and NOQ powerfully inhibited 3H-thymidine uptake at a concentration of 10 µM, a concentration at which the other compounds exhibited comparatively slight inhibitory effects.

Experiments with H9 cells grown in 10% fetal bovine serum (FCS) (FIG. 2B) found NOQ to be the most potent inhibitor, demonstrating almost complete inhibition at 10 µM levels. MOBP demonstrated about a 30% decrease in thymidine uptake at 10 µM, and an almost complete inhibition of uptake at 100 µM. NOBA demonstrated about 75% level of inhibition at 10 µM, about 85% inhibition at 100 µM, and almost complete inhibition at 250 µM. The remaining amino and nitro compounds were significantly less potent and did not display complete inhibition until concentrations of 1000 µM were reached.

Experiments with K562 cells grown in 10% fetal bovine serum (FIG. 2D) found NOQ and NOBP to be the most potent inhibitors of cell growth. Both NOQ and NOBP resulted in the almost complete inhibition at concentrations of 10 µM. NOBP was almost as potent as NOQ and produced about 90% inhibition at a concentration of 10 µM, and almost complete inhibition at a concentration of 100 µM. The other 3 compounds tested were significantly less potent.

Experiments with 855-2 cells grown in 10% fetal bovine serum (FIG. 2A) found that NOQ, and NOBP produced almost complete inhibition at a concentration of 10 µM. At a concentration of 1 µM, NOQ produced somewhat more inhibition than NOBP, and NOBP produced somewhat more inhibition than NOBA. Experiments using HL-60 cells (FIG. 2C) provided similar conclusions. The other 3 compounds tested were significantly less potent.

The effect of different growth factors on the growth inhibitory effects of NOBP was tested. 855-2 cells that were grown in media with (1) 10% fetal bovine serum, (2) autocrine growth factor (AGF) and (3) low molecular weight-BCGF (a T cell derived lymphokine) were exposed to increasing concentrations of the ADRPT ligands. The results are provided in FIG. 2(A, E, F). Cells grown in each of the growth factors were all potently inhibited by the nitroso-containing compounds, with concentrations of 5 to 10 µM resulting in 100% inhibition. Thus, NOBP, NOBA and NOQ exert potent inhibitory effects regardless of the source of growth factor activity.

Figure 3:
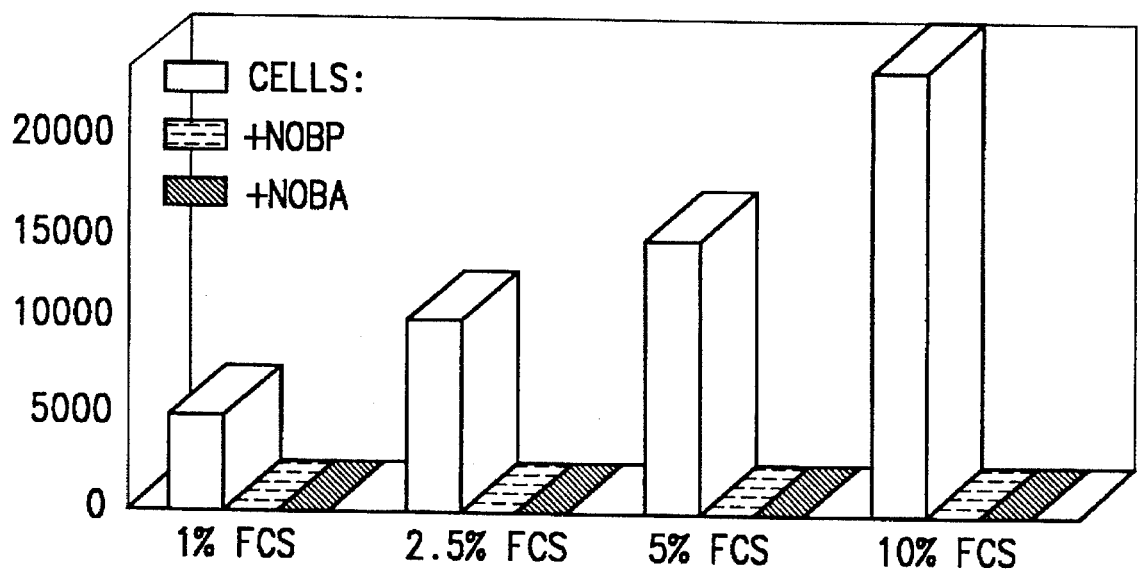
FIG. 3 is a graph showing the inhibition of increasing levels of leukemic cell growth (in response to increasing concentrations of FCS) of 855-2 cells by 6-nitroso-1,2-benzopyrone (NOBP) and 3-nitrosobenzamide (NOBA).
Figures 5A, 5B:
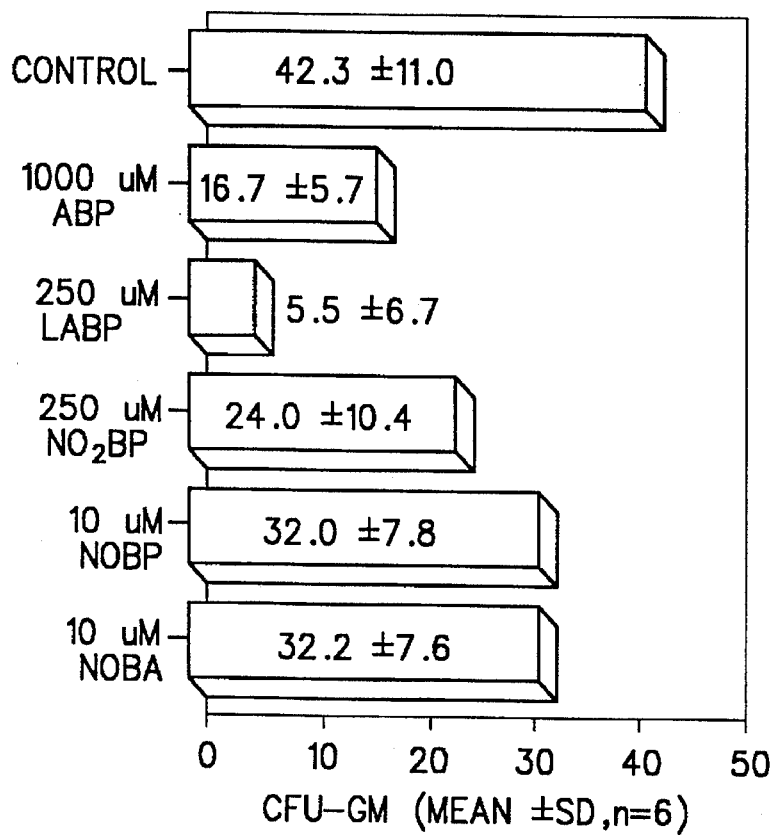
FIGS. 5A–5B show graphs of the relative inhibitory effects of anti-leukemic doses of ADRPT ligands on the ability of (FIG. 5A) normal rhesus bone marrow stem cells or (FIG. 5B) human peripheral blood stem cells to form colonies in soft agar. Note that the NOBP and NOBA had minimal effect on normal cells.
Figure 8:
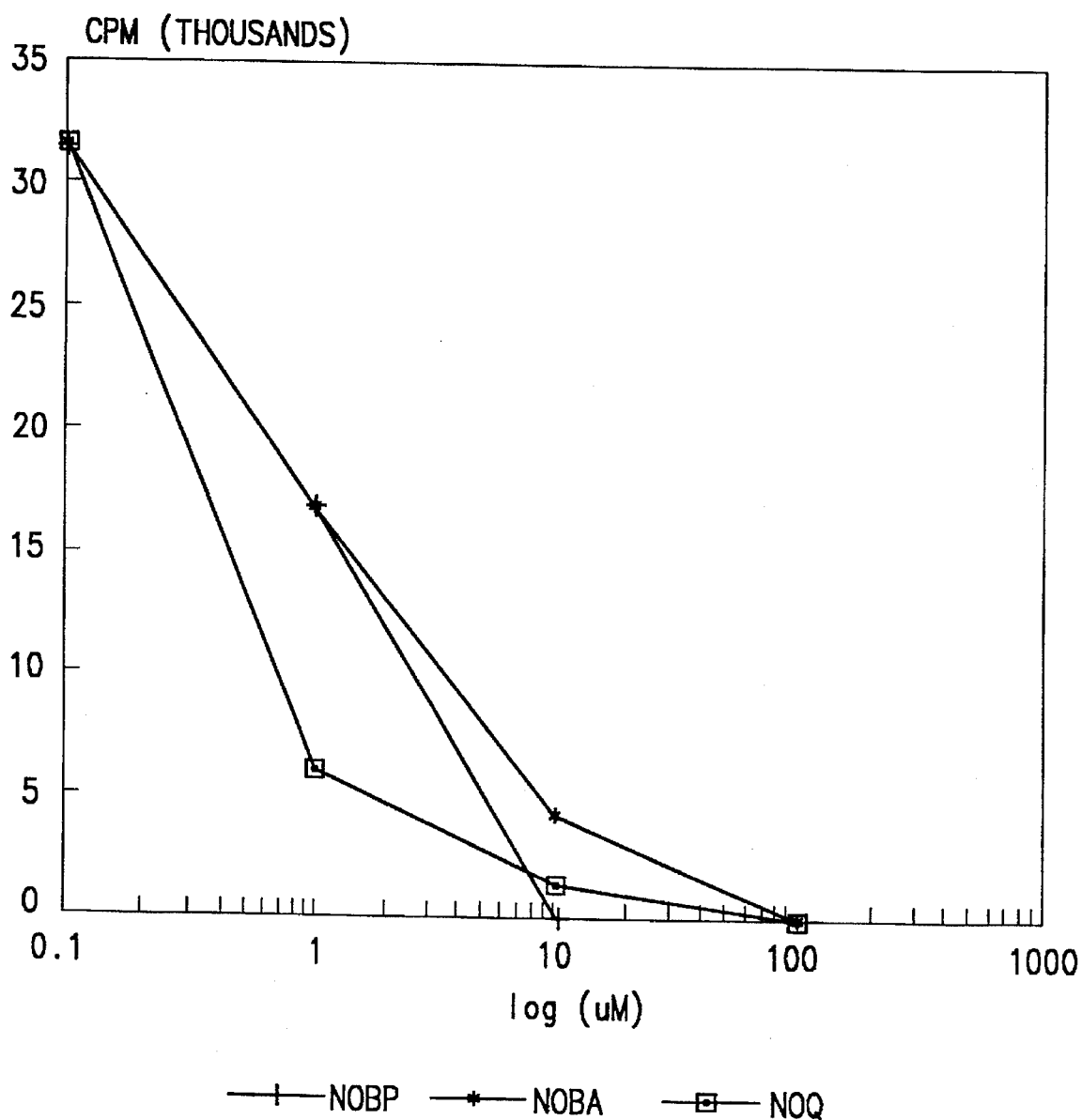
FIG. 8 is a graph displaying the effects of NOBP, NOBA and NOQ on human breast tumor cell line MDA 468.
Figure 9:
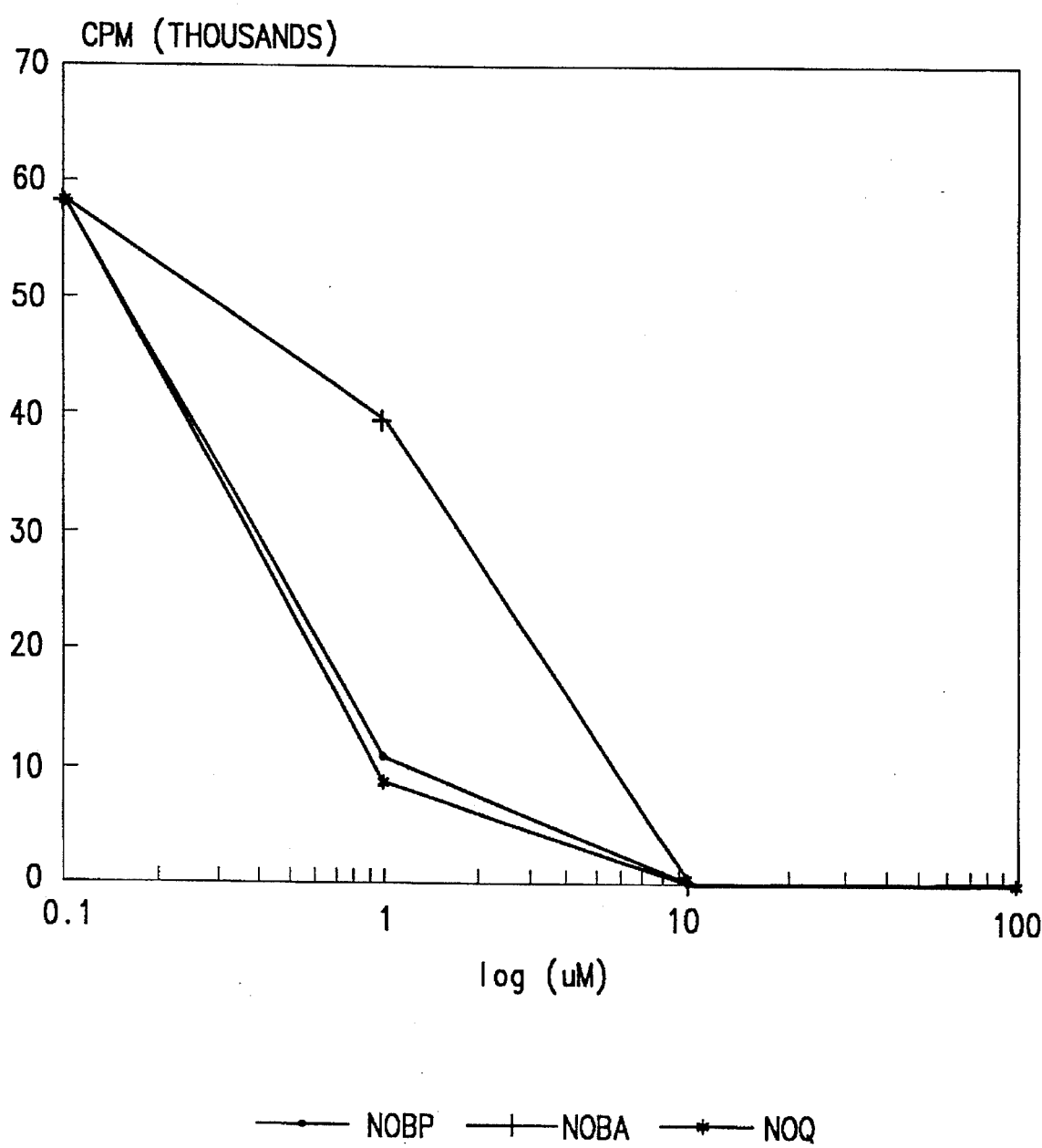
FIG. 9 is a graph displaying the effects of NOBP, NOBA and NOQ on murine leukemia cell line L 1210.

In order to exclude the possibility that NOBP and NOBA manifest their growth inhibitory effects through inactivation of growth factors, the effects of 10 µM NOBP or NOBA (constant concentration) on 855-2 cells in the presence of increasing concentrations of fetal bovine serum (FCS) were tested (FCS) contains growth factors for 855-2 cells). The data are provided in FIG. 3. Growth arrest occurs irrespective of the concentration of FCS. Thus, the mode of action of NOBP, does not appear to be by antagonism of growth factors but at ADPRT sites related to DNA-replication.

In preliminary experiments the propagation of L1210 murine leukemia was also tested in vivo and the results showed that NOBA injected intraperitoneally at a dose of 2 mg/kg twice a day for 6 consecutive days, causing no toxic effects, prolonged the life of BDF mice from 10 days (untreated) to 35 days (end of observation), thus exerting a highly significant in vivo chemotherapeutic response. These results are somewhat surprising in light of the high levels of ascorbic acid present in mice. Ascorbic acid, a strong reducing agent, reduces 3-NOBA. In its reduced form 3-NOBA is not as effective at removing zinc from zinc fingers. Hence, one would not expect 3-NOBA to be as an effective chemotherapeutic agent in the presence of high levels of ascorbic acid.

Tumor cell inhibitory concentrations of NOBP and NOBA were shown not to affect adversely the viability of normal cells. Experiments were performed in which the functions of various cancer cells (855-2 and HL-60 leukemia cells, D32, D37 and CRL 7712 glioblastoma cell lines, 186 medulla tumor cell line, L1210 murine leukemia cell line, MDA-468 human breast tumor cell line) and normal cells (neutrophil leukocytes and bone marrow or peripheral blood stream cells) were assessed in the absence or presence of the compounds. The results are shown in FIGS. 4–9. Together, the data indicate that a concentration of 10 µM of the nitroso-containing ligands effectively suppressed cancer cell growth but demonstrated only modest effects the functions on normal cells.

VI. Toxicity of NOBP

The cytotoxicity of 0, 2 µM, 4 µM, 8 µM and 10 µM NOBP was measured by examining the effect of the compound on the colony formation (CFU-GM) of normal human stem cells (PBSC). The results of the experiments are provided in FIG. 5B. Toxicity was not detected, even though levels of NOBP sufficient to block 855-2 cell proliferation completely were tested.

A similar CFU stem cell toxicity assay was performed in which comparisons were made between (ABP) 6-amino-1,2-benzopyrone 1 mM, (IABP) 5-I-6-amino-1,2-benzopyrone 250 µM, ($NO_2BP$) 6-nitro-1,2-benzopyrone (weakly active) 250 µM, NOBP 10 µM, and NOBA 10 µM. The results of the experiments are provided in FIG. 5A. Whereas the 6-amino-1,2-benzopyrone, 5-I-6-amino-1,2-benzopyrone and the 6-nitro derivative were toxic at the tested given doses, the almost ineffective (against tumor cells) 6-nitro derivative and the highly effective (against tumor cells) NOBP and NOBA were non-toxic.

The effects of 10 µm NOBP and NOBA on superoxide generation by normal human peripheral blood neutrophil leukocytes was tested. The results are provided in Table II. Only minor reductions in superoxide generation were observed.

TABLE II

Effects of 10 μM NOBP and NOBA on the Generation of Superoxide by Human Neutrophils

| | nmol $O_2^-$/hr/$10^5$ cells (mean ± S.D., n = 11) |
|---|---|
| $10^5$ PMN + PMA: | 55.9 ± 7.7 |
| +10 μM NOBP | 34.1 ± 14.1 |
| +10 μM NOBA | 44.4 ± 10.0 |

VII. Comparative Efficacy Studies

Vincristine, a highly toxic chemotherapeutic compound, is currently used in the treatment of leukemia and other malignancies. Studies were performed in order to determine the concentration of vincristine that produces the same level of growth inhibition as 10 μM NOBP, when assayed on 855-2 leukemia cells grown in vitro. Vincristine was tested in doses of 0.1, 1, 10 and 100 μM. As shown in FIG. 7. 100 μM of vincristine (a highly toxic concentration) was required to produce the same level of inhibition as 10 μM of NOBP, thus NOBP is about 10 times more potent than an equal concentration of vincristine, and is not toxic to normal cells.

Thus certain aromatic nitroso molecules that are also inhibitors of ADPRT polymerase activity may be useful chemotherapeutic cytostatic agents because of their effectiveness combined with low toxicity.

VIII. Anti-HIV action of NOBP, NOBA and NOO on Stimulated Human Lymphoblasts The ability of NOBP (6-nitroso-1,2-benzopyrone) and NOBA (3-nitrosobenzamide) to inhibit HIV infections were tested using the methods described in the *Journal of Immunological Methods* 76: 171–183 (1985). Exposure to the two drugs was only for 30 minutes at the commencement of viral infection, and drugs were never re-added. The results given in Table III provide the $ID_{50}$ of HIV titer 10 days after infection of cell cultures with HIV. The data in Table III demonstrate that 10 μM of the nitroso-containing ligands causes a three log decrease in the HIV-1 infectivity titer.

TABLE III

| Test Sample | Virus Titer (log $ID_{50}$) 10 days |
|---|---|
| Virus Alone | 5.25 |
| +500 μM ABP | 4.50 |
| +250 μM IABP | 4.66 |
| +250 μM $NO_2$BP | 4.93 |
| +10 μM NOBP | 2.01 |
| +10 μM NOBA | 1.05 |
| +10 μM NOQ | 1.73 |

IX. Cytocidal Activity of ADRPT Ligands—MTT Assay

Experiments were performed to determine if the inhibition of proliferation of 855-2 cells seen in culture and in soft agar is due to the cytostatic or cytocidal effect of the nitroso compounds NOBP, NOBA, and NOQ. Cells at $1 \times 10^5$/ml (concentration used in bone marrow assay) were treated with NOBP, NOBA and NOQ at 1, 2.5, 5 and 10 μm for 2 hours then stimulated with 10% fetal calf serum and incubated for 24 hours. MTT (3-[4,5-Dimethyl-2-yl]-2,5-diphenyltetrazolium bromide) at 1 mg/ml was then added for 16 hours. The absorbance of the pelleted cell was then measured at 550 nm after adding DMSO to solubilze the cells.

Results: With 10 μM NOBP, NOBA and NOQ, complete killing was observed in 855-2 cells at 100,000/ml.

X. NMR Studies of $Zn^{+2}$ Ejection from Zn (HIV1-F1)

Figure 10:
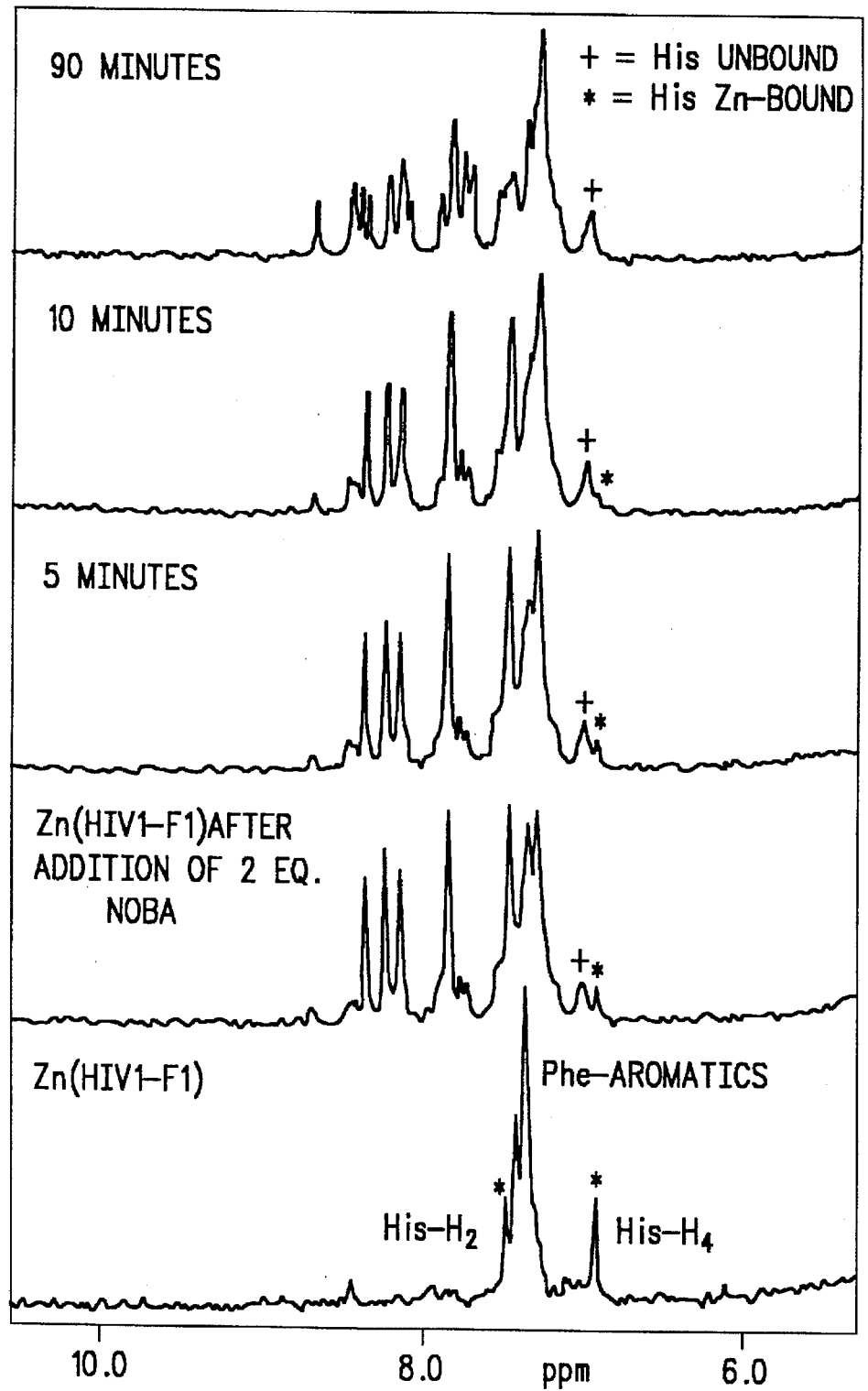
FIG. 10 shows the downfield region of the $^1H$ NMR spectrum obtained for Zn (HIV1-F1)(1 mM in $D_2O$ solution, pH=6.2, T=30° C.)(bottom) and upon addition of NOBA (2 mM). The * and + symbols denote the aromatic proton signals of the zinc-coordinated and zinc-free His 9 residue. Upon completion of the reaction, reflected by complete ejection of zinc (t=90 min), 50% of the NOBA remained unreacted indicating a 1:1 reaction stoichiometry. NOBA (3-nitrosobenzamide), was synthesized described elsewhere in this application.

To determine if NOBA is capable of ejecting zinc from retroviral-type zinc fingers, NMR studies were performed on a peptide with amino acid sequence corresponding to the N-terminal CCHC zinc finger of the HIV-1NC protein, Zn (HIV1-F1), South, et al., *J. Am. Chem. Soc.* 111: 395–396 (1989), South, et al., *Biochem Pharm.* 40: 123–129 (1990), Summers, et al., *Biochemistry* 29: 329–340 (1990). NMR spectra of Zn (HIV-F1) were performed before and after the addition of NOBA (3-nitrosobenzamide). Previous NMR studies have demonstrated that this peptide binds zinc stoichiometrically and with high affinity, South, et al., *J. Am. Chem Soc.* 111: 395–396 (1989), and three-dimensional structural studies have shown that the peptide adopts a structure that is essentially identical to the structure of the corresponding region in the intact NC protein, South, et al., *Biochemistry* 29: 7786–7789 (1990). NMR spectra of Zn (HIV-F1) were performed before and after the addition of NOBA (3-nitrosobenzamide). The down-field region of the $^1$H NMR spectrum showing the signals due to the aromatic proton of His 9 and Phe 2 is illustrated in FIG. 10 (bottom). Addition of two molar equivalents of NOBA results in the loss of the signals due to zinc-bound histidine (denoted by *) and the appearance of broad signals representative of zinc-free histidine (denoted by +). Other signals in the spectrum are due to NOBA protons. After 90 min., no signals attributable to the zinc-bound His could be detected, see FIG. 10. After 90 minutes, the signals due to unreacted NOBA were of equal intensity compared to the reacted NOBA signals, indicating that NOBA reacts stoichiometrically with Zn (HIV1-F1); this finding has been confirmed by additional studies with one equivalent of NOBA. By comparison, a 10-fold molar excess of EDTA is required to remove zinc from Zn (HIV-1-F1), Summers, et al., *J. Cell Biochem* 45: 41–48 (1991).

XI. NMR Studies of Zn (HIV1-F1) Nucleic Acid Binding

Figure 11:
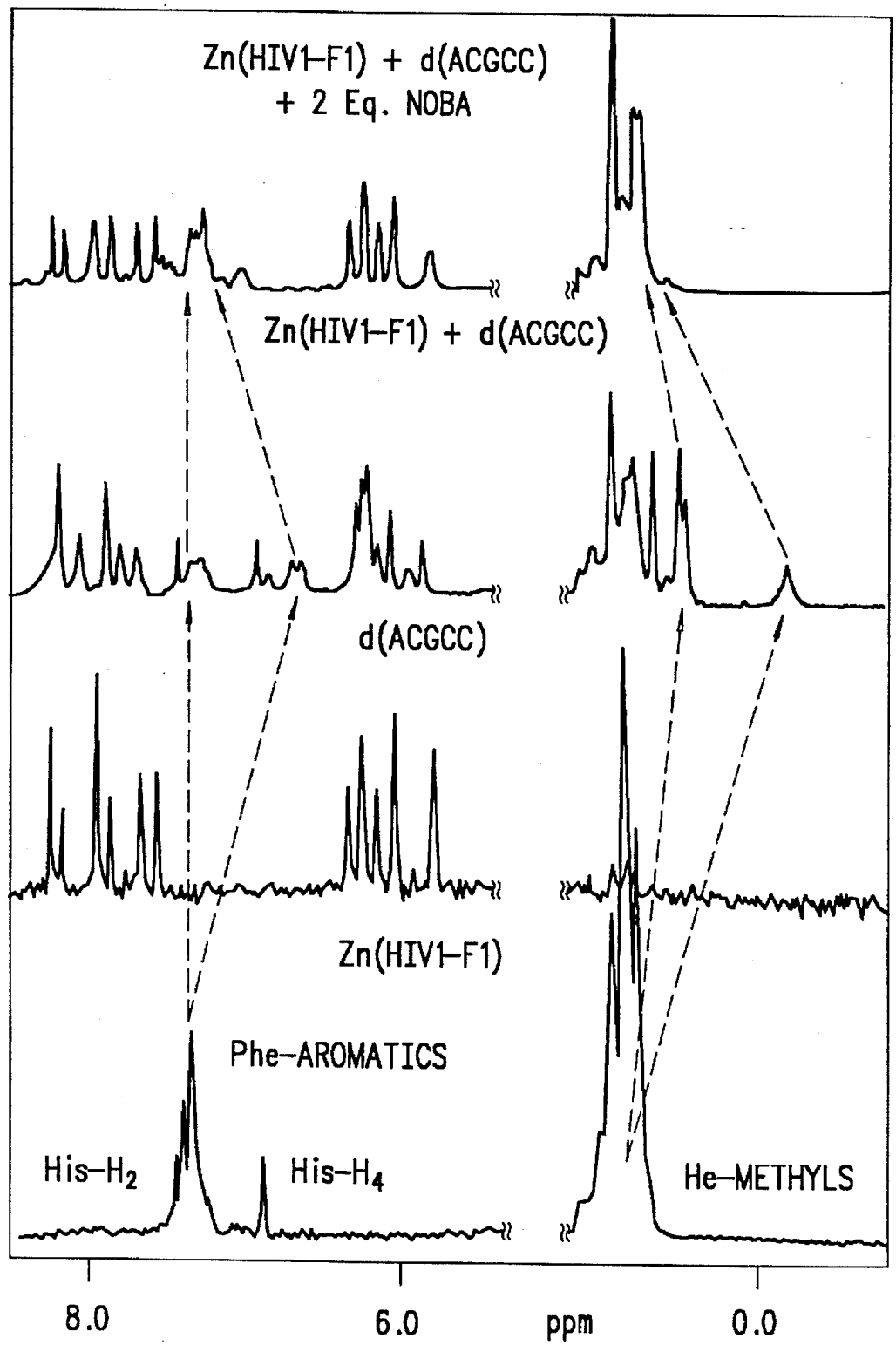
FIG. 11 shows selected regions of the $^1H$ NMR spectrum obtained for Zn (HIV1-F1)(bottom) and a synthetic oligonucleotide with sequence corresponding to a region of the HIV-1 Psi-packaging signal, d(ACGCC)(2nd from bottom). The downfield regions of the spectra show the signals of the aromatic and ribose H1' protons, and the upfield region contain signals of the methyl group protons. Dramatic spectral changes occur upon addition of oligonucleotide to Zn (HIV1-F1), including large upfield shifts of the Phe 2 and Ile 10 side chain=n signals and a downfield shifting and broadening of the guanosine-H proton signal (second from the top). After incubation with two equivalents of NOBA, the spectral features are characteristic of metal-free peptide and dissociated nucleic acid (top), indicating that NOBA-induced zinc ejection leads to loss of high-affinity nucleic acid binding function.
Figure 12:
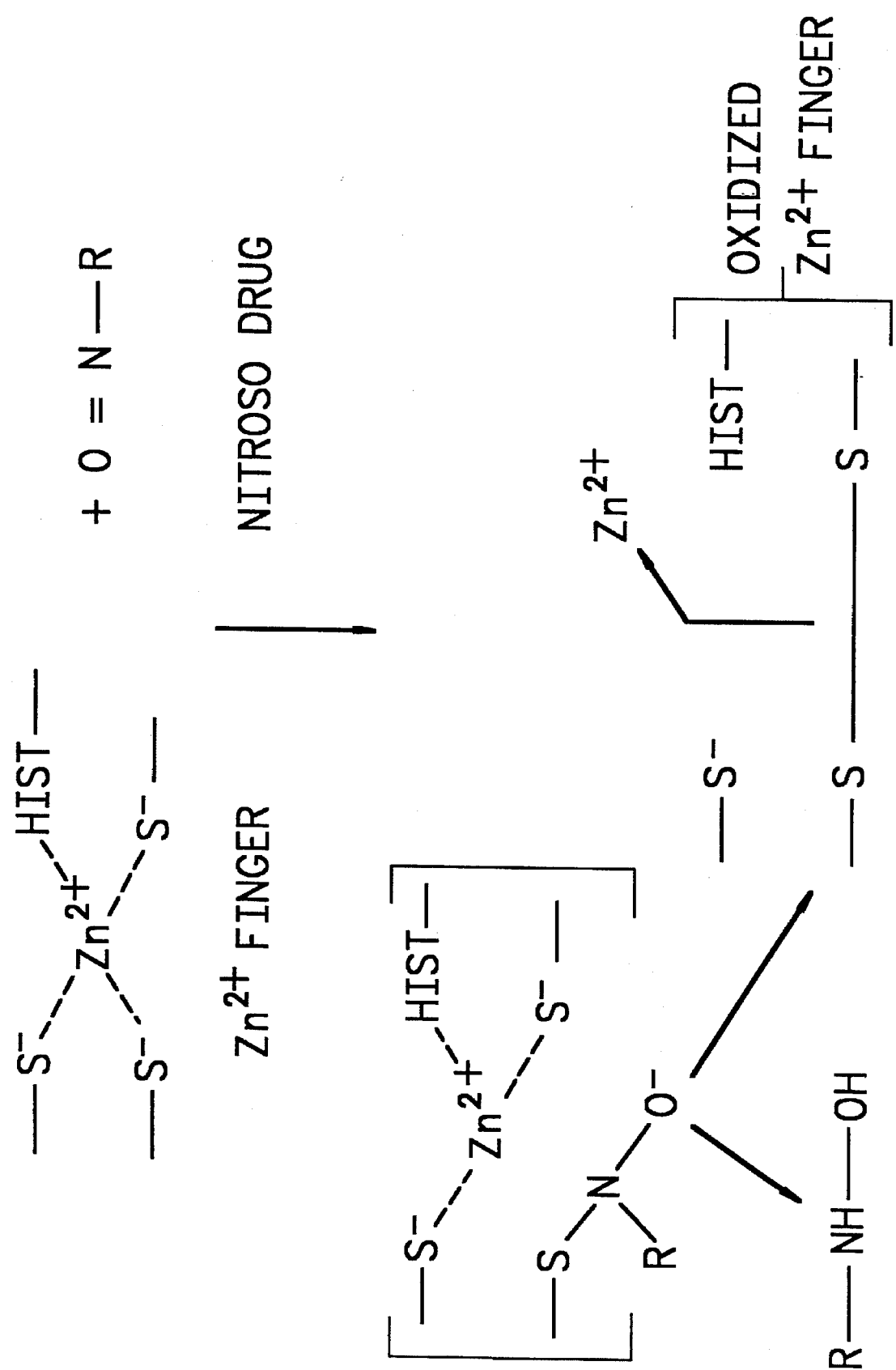
FIG. 12 shows the proposed mechanism for the ejection of $Zn^{+2}$ from Zn (HIV1-F1) by NOBA (3-nitrosobenzamide).

Zn (HIV1-F1) has been shown to bind to single-stranded nucleic acids with sequence specificity, and a highly stable complex with a 5-residue oligonucleotide, d(CACGCC), containing the sequence of a portion of the HIV-1 Psi-packaging signal has been prepared for high-resolution structural studies. Experiments have been performed indicating that the addition of NOBA to this protein-oligonucleotide complex results in ejection of zinc with concomitant dissociation of the zinc finger nucleic acid complex, (FIG. 11). These data indicate that the CCHC array ($Cys-X_2-Cys-X-His-X_4-Cys$) of the HIV-1NC protein Zn (HIV1-F1) can be specifically affected by NOBA so that functional binding to nucleic acid substrates is abated. The reaction mechanism, schematically illustrated in FIG. 12, is consistent with the result of NMR analysis in FIGS. 10 and 11. The reaction mechanism proposed in FIG. 12 is a useful model but is not intended to limit the scope of the claimed invention.

XII. Zinc Loss Resulting from Treatment of HIV-1 Virions with NOBA

Experiments were performed to determine if NOBA is capable of ejecting zinc from intact virions. HIV-1 (MN strain) was produced, purified and concentrated as described in Bess et al., *J. Virol.* 66: 840–847 (1992). The concentrated virus was diluted to 60 times that of culture fluid in TNE buffer (0.01M Tris-HCl, 0.1M NaCl, 1 mM EDTA, pH 7.2) and incubated with 3000 or 6000 µM NOBA at 37° C. The virus was then pelleted and washed with TNE buffer to remove weakly bound zinc. The quantity of zinc in the resulting viral pellets was determined as described in Bess et al., *J. Virol.* 66: 840–847 (1992). No significant loss of viral proteins in the pellet was detected by p24 and gp120 competition radioimmunoassays and comassie-stained sodium dodecyl sulfate polyacrylamide gel electrophoresis.

The data in Table IV demonstrate that treatment of concentrated suspensions of HIV-1 (60× with respect to culture solution) with NOBA results in losses of 50–83% of the viral zinc and complete loss of infectivity. Since edge x-ray absorption fine structure spectroscopy has shown that the majority of the zinc in intact retroviruses is coordinated by the CCHC ligands (Summers, et al., *Protein Science* 1: 563–574 (1992) and Chance et al., *Proc. Natl. Acad. Sci.* 89: (1992) in press)), the ejection of zinc from virions by NOBA is directly attributable to a destabilization of the nucleocapsid CCHC zinc fingers. Anti-HIV activity for R—$NH_2$ type ligands of poly (ADP-ribose) polymerase (Cole et al., *Biochem. Biophys. Res. Commun.* 180: 504–514 (1991)) may now be attributed, in part, to destabilization of retroviral CCHC zinc fingers since R—$NH_2$ compounds are metabolic precursors of R—NO type molecules (Buki, et al., *FEBS 2Lett.*, 290: 181–185 (1991)).

TABLE IV

| NOBA (µM)[b] | Incubation time (h) | Zinc, Control Sample (µg/ml) | Zinc, NOBA-Treated Sample (µg/ml) | Zinc Loss (%) |
| --- | --- | --- | --- | --- |
| 3,000 | 2 | 0.21 | 0.11 | 52 |
| 6,000 | 4 | 0.24 | 0.04 | 83 |

[b]Concentrations correspond to molar NOBA:zinc finger ratios of ca. 350:1 (3,000 µM) and 700:1 (6,000 µM)

XIII. In Vivo Testing of NOBP and NOBA

Figure 13A:
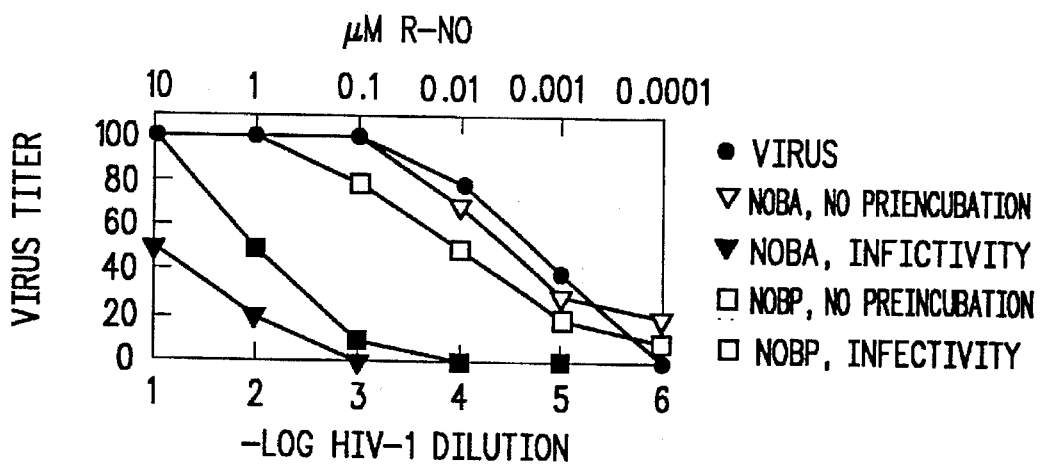
FIG. 13 A. shows the HIV-1 inactivation assay using NOBA and NOBP (6-nitroso-1,2-benzopyrone). The HIV-1 stock (HIV-1 100,000 $TCID_{50}$ was treated for 30 Min. with 100 µM NOBA or 100 µM NOBP at 22° C., the mixture was serial 10-fold diluted and inoculated into PBL cultures. After 9 days the culture supernatants were harvested and the frequency of infected cultures was measured by immunoassay. The percent positive of cultures was then plotted as a function of the virus input titer. The relative amount of infectious virus available to cause 50% infected cultures was decreased by 4 log units with NOBA. NOBP was synthesized by the methods described below.
Figure 13B:
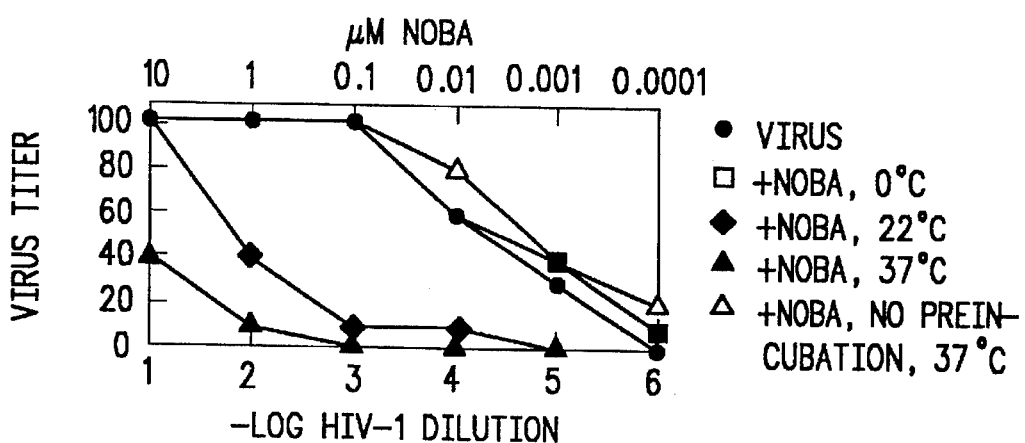
Figure 13C:
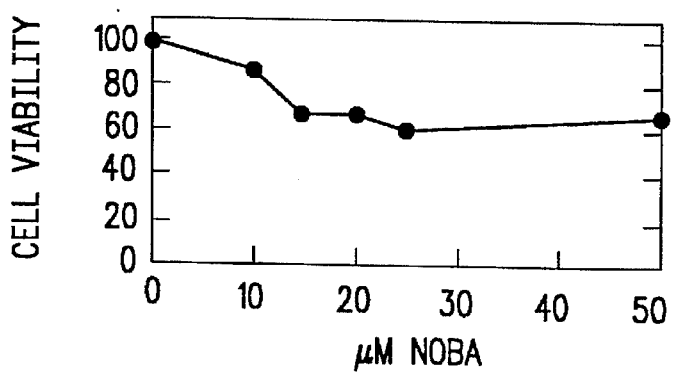

Both NOBP (6-nitroso-1,2-benzopyrone) and NOBA were tested on viral growth of HIV-1 (LAV strain) in phytohemagglutinin-stimulated human peripheral lymphocytes (PBL) as follows. An HIV-1 stock having an infectivity titer of 100,000 $TCID_{50}$ was incubated for 30 min. at 22° C. with either of the drugs. Control HIV samples, containing no drugs, were incubated in the same manner. Following successive serial dilutions of 10-fold that resulted in HIV-1 titers as giver in the lower abscissa of FIG. 13 (A,B), viral growth was initiated by adding the HIV-1 dilutions to PBL and allowing an incubation period of 9 days. At the end of this incubation cultures were assayed for productive infection by an immunoassay for HIV-1 antigens and by reverse transcriptase as described in McDougal, et al., *J. Immunol Methods* 76: 171–183 (1985). Virus titers were expressed as percentile values (percent infected cultures) compared to the controls, containing HIV dilutions which were not preincubated with the C-nitroso drugs. In a separate series of experiments, HIV-1 dilutions and C-nitroso drugs (see upper abscissa) were not preincubated but were added simultaneously to lymphocytes in exactly the same concentrations as described previously (i.e., following preincubation) and viral growth monitored 9 days later. As illustrated in FIG. 13, South, et al., *J. Am. Chem. Soc.* 111: 395–396 (1989), South, et al., *Biochem Pharm.* 40: 123–129 (1990), Summers, et al., *Biochemistry* 29: 329–340 (1990), the inhibition of HIV-1 propagation was profound when C-nitroso drugs were preincubated with HIV-1, whereas only negligible effect on HIV-1 growth occurred when both drugs and virus were added simultaneously. Between the two C-nitroso drugs, NOBA induced a greater depression of HIV-1 propagation.

Experiments were performed in which the incubations with NOBA was carried out at 0°, 22°, and 37° C. From FIG. 13B it is apparent that inactivation of HIV-1 by NOBA occurred maximally at 37° C., suggesting a probable lesser accessibility of the viral zinc finger to the drugs as compared to the Zn (HIV-1-F1) present in the isolated polypeptide (FIGS. 10 and 11). In agreement with the negligible cytotoxic effect of C-nitroso drugs on non-tumor cells described elsewhere in this application, human lymphocytes tolerated NOBA up to 50 µM without major changes in cell metabolism, which was assayed by quantitative dye reduction as described in Mosaran, *J. Imm. Methods* 65: 55–63 (1983).

The direct action of C-nitroso drugs on a critical molecular structure of the HIV-1 virus itself, the zinc finger of NC protein, distinguishes these drugs from any presently known chemotherapeutic agents. Metabolic precursors of C-nitroso drugs, which are R—$NH_2$ type ligands of poly (ADP-ribose) polymerase, suppress HIV-1 replication of both MT-2 an Aa-2 cells, Cole, et al., *Biochem. Biophys. Res. Comm.* 10: 504–514 (1991). Correlation between the inhibitory binding of these R—$NH_2$ ligands to poly (ADP-ribose) polymerase and their anti-HIV effectively indicates the participation of this nuclear enzyme in the mode of action of these molecules as antiviral agents. However the concentration of the R—$NH_2$ drugs required to block HIV-1 replication is about $10^3$ higher than the effective antiviral concentration of C-nitroso drugs. Considering the relatively slow rate of the oxidation of R—$NH_2$ drugs to C-nitroso molecules (Buki, et al., *FEBS Letters* 290: 181–185 (1991)) in cells, the relatively high concentrations (millimolar) of R—$NH_2$ drugs correspond to their role as "pre-drugs" or sources of C-nitroso type molecules which are effective in micromolar concentrations. Therefore a direct action of C-nitroso drugs formed from their precursors is feasible, although it cannot be ruled out at present that these drugs, besides acting directly on HIV-1 as shown here—may have an additional mode of action that could be related to the effects of C-nitroso drugs as apoptosis-inducing agents in cancer cells.

XIV. Inhibition of the Replication of Native and 3'-Azido-2',3'-Dideoxythymidine (AZT)-resistant Simian Immunodeficiency Virus (SIV) by 3-NOBA CEM x174 cells are the fusion product of human B cell line 721.174 and human T cell line CEM (12). A molecular clone of $SIV_{mac}(SIV_{mac}239)$ was kindly provided by Dr. R. Desrosiers of the New England Primate Research Center. AZT (3'-azido-2',3'-dideoxythymadine) was manufactured by the Burroughs Wellcome Co. The compound 3-nitrosobenzamide (NOBA) was synthesized as described in example II. RPMI 1640 supplemented with L-glutamine was purchased from Gibco Labs, Inc.

Preincubation with the 3-NOBA

CEM x174 cells were suspended at $4 \times 10^5$ cells/ml and distributed into 23-well tissue culture plates. Cultures were treated with various concentrations of the test compound (along with DMSO as controls) and incubated at 37° C. for 1 hr in a $CO_2$ incubator. The cells were infected with 5 µl of a stock solution of $SIV_{mac}239$ at 300 $TCID_{50}$/ml (50% tissue culture infectious dosage per ml cell suspension). Cell viability was determined by the tetrazolium salt (MTT) assay and the cultures were divided 1:4 every 3–4 days in medium containing the drug. The cultures were examined periodically by light microscopy for the presence of syncytia. The virus titers were determined by analysis of supernatant SIV p27 core antigen protein or reverse transcriptase (RT) levels.

Preincubation with the Virus

CEM x174 were distributed into 24-well tissue culture plates as above. Cells were incubated with virus for 2 days (until syncytia appeared) before treatment with NOBA. Cultures were examined periodically for the presence of syncytia. Virus titers were determined by SIV p27 or RT assays.

Reverse Transcriptase Assays

To test for reverse transcriptase activity, 10 μl of infected cell supernatant was added to a reaction mixture containing 50 mM tris-HCL (pH 8.0), 5 mM $MgCl_2$, 10 mM dithiothreitol (DTT), 20 mM KCl, and 1% Triton X-100 in a total volume of 50 μ. Poly(rA)oligo(dT)$_{12-18}$ was present at 100 μg/ml and TTP at 2.4 μM. The reaction mixtures were incubated at 37° C. for 1 hr and the TCA precipitable radioactivity was filtered onto nitrocellulose filters which were then washed, dried, and counted.

Tetrazolium Salt (MTT) Assays

Cell viability was measured by a published procedure. Hansen et al. *J. Immunol Methods* 119: 203–210 (1989). Briefly, MTT (3-(4,5-dimethylthiazol-2-yl)-2,5-diphenytltetrazolium bromide) was dissolved at a concentration of 5 mg/ml in sterile phosphate buffered saline (PBS). Twenty μl of MTT solution were added into each microtiter well containing 100 μl of cell culture. Following 2 hr incubation at 37° C., 100 μl of solubilizing medium (cf. 13) were added. After overnight incubation at 37° C., optical densities were measured at 570 nm using a microtiter plate reader.

$SIV_{mac}$ p27 core antigen level was determined by an enzyme immunoassay provided by Coulter Corp. (Hialeah, Fla.). The assay was performed according to the manufacturer's specifications.

Polymerase Chain Reaction (PCR) Analysis of Infected Cell Genomes

DNA extracted from drug-treated, SIV-infected CEM x174 cells or from control cells were screened for the presence of the SIV sequence by a published method using individually-designed primers corresponding to the SIV gag gene. Blackbourn et al., *J. Virol Methods* 37: 109–118 (1992). Northern hybridization has shown the primers to be complementary to the region encoding the major core antigen protein p27.

Assays on human lymphocytes were performed as described in Example XIII.

Figure 14A:
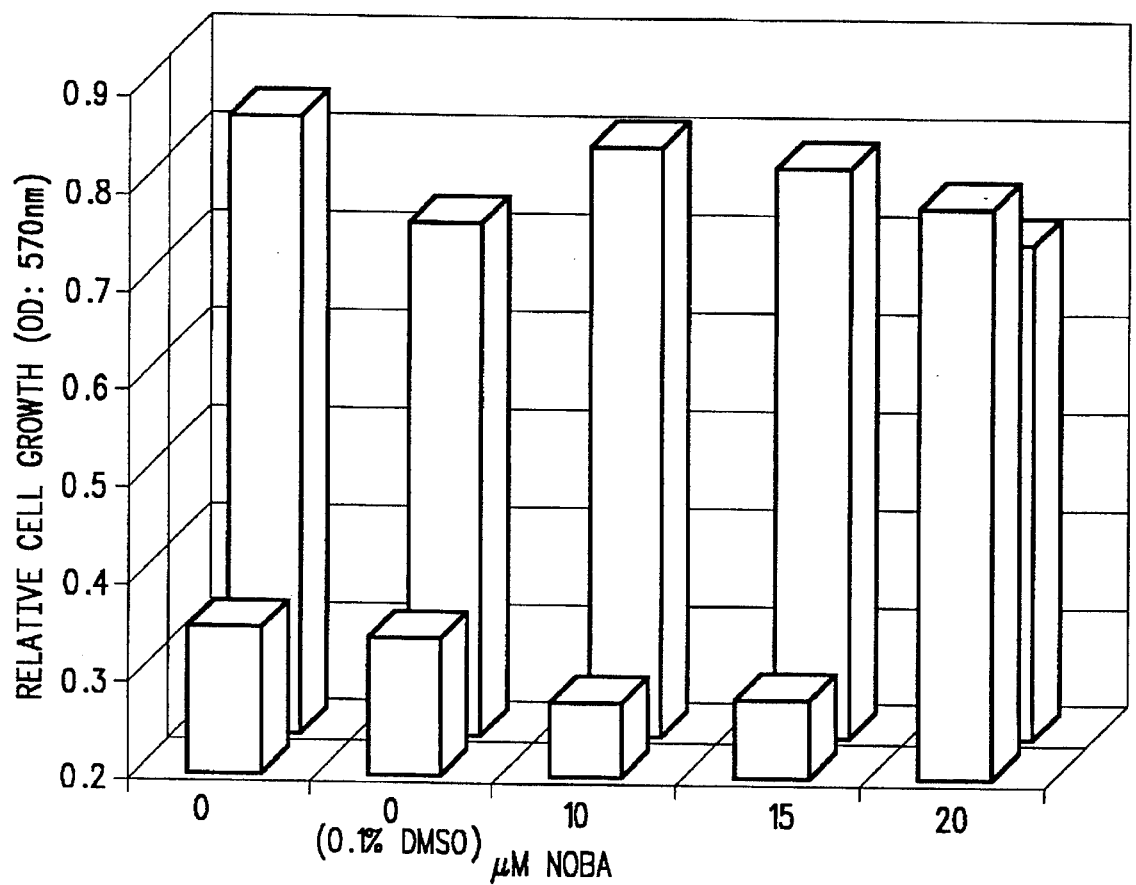
FIGS. 14A–B. The effect of NOBA on $SIV_{mac}239$ replication (FIG. 14A) and CEM x174 cell viability (FIG. 14B). Each bar expresses the means of 3 independent tests, which do not differ ±10% (not shown).
Figure 14B:
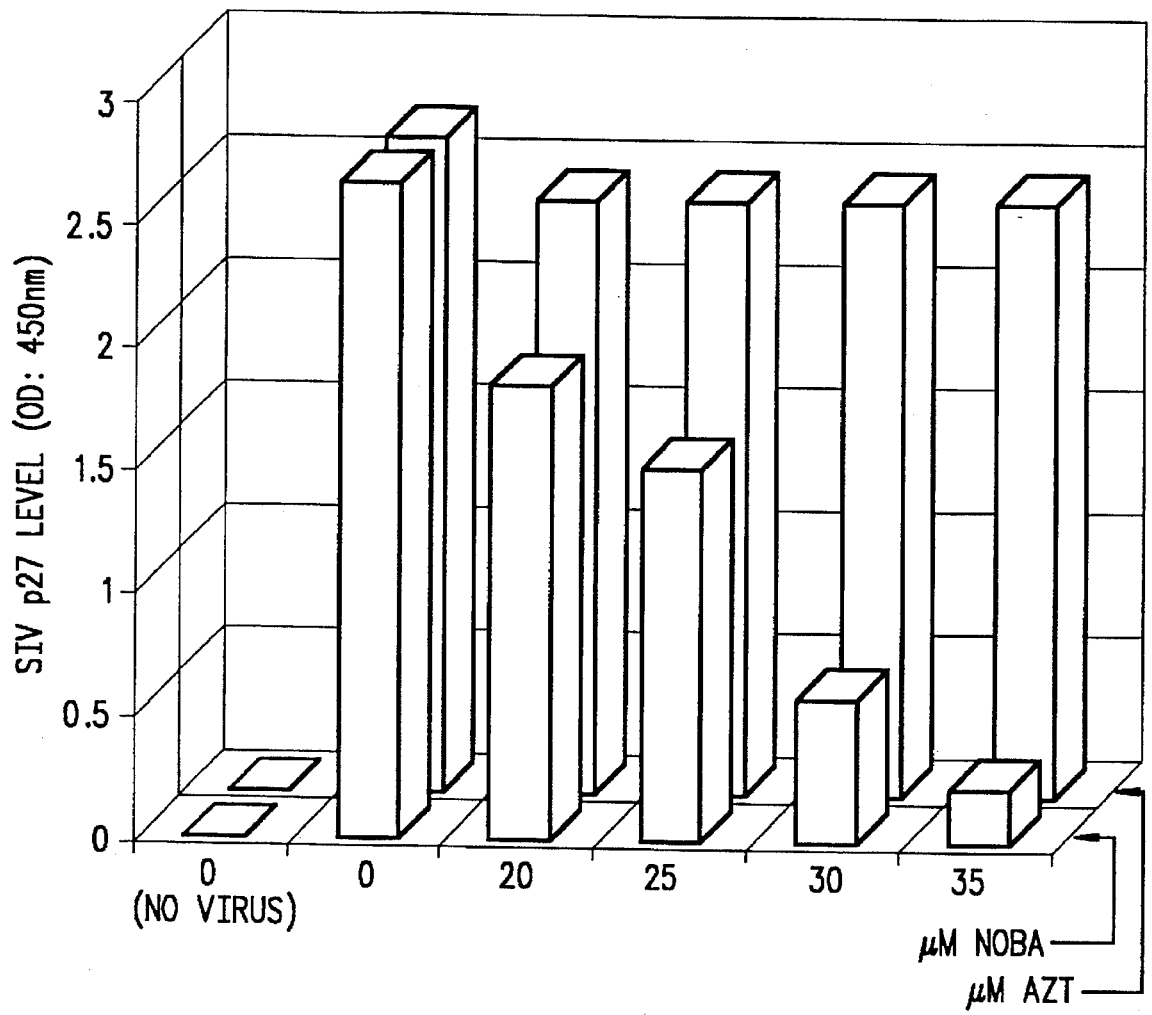

The effectivity of NOBA in preventing $SIV_{mac}239$ replication in CEM x174 cells was determined by preincubating cells in varying concentrations of NOBA at 37° C. for 1 hr before infection with the virus. As illustrated in FIG. 14A, pretreatment of CEM x174 cells with 0 to 20 μM NOBA and maintenance of these drug concentrations during the entire experimental period strikingly abolished $SIV_{max}239$ replication only at 20 μM NOBA, no effect NOBA was detected at lower drug concentrations. The exact reasons for the sharp transition between ineffective (below 15 μM) and fully effective (20 μM) NOBA concentrations are not known, but it is possible that the quantity of intracellular NOBA-inactivating systems may explain this phenomenon, which is overcome by higher than 15 μM NOBA. Coincidental with the antiviral action of 20 μM NOBA cell viability was maintained at the level of virus-free controls (FIG. 14B). However, when SIV p27 levels were high the cytocidal action of $SIV_{mac}239$ was reflected in a significantly depressed cell viability, as would be predicted.

Figure 15A:
FIGS. 15A–B. Analysis of the cellular genome of SIV-infected and uninfected cultures by PCR. CEM x174 cells from 6-day cultures of the experiment described in FIGS. 14A–B were used for DNA extraction. (Six-day cultures were used instead of 10-day cultures to ensure the presence of enough extractable DNA).
Figure 15B:
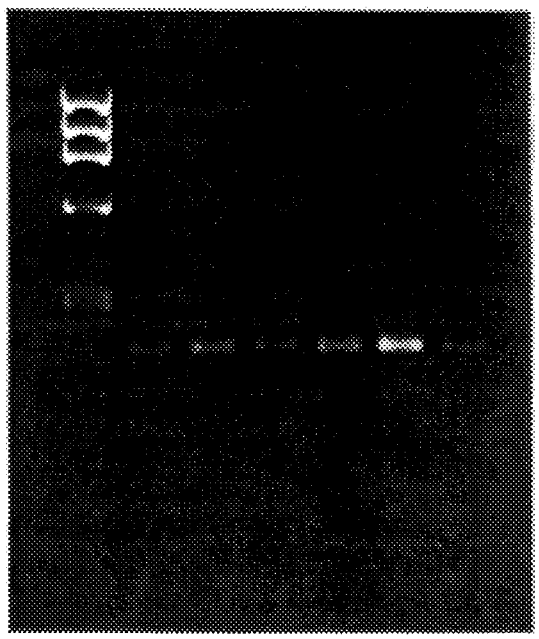

Since virus replication as expected to coincide with the appearance of integrated viral DNA in the genome of CEM X174 cells, cellular DNA was assayed by the polymerase chain reaction (PCR) method with the aid of specifically designed gag-selective SIV primers. Blackbourn et al., J. Virol Methods 37: 109–118 (1992). Results of the PCR assay are shown in FIGS. 15A–B. Lane 1 in FIG. 15A is a molecular marker (Hind III digested φX 174 DNA), and Lane 2 is the plasmid DNA encoding the SIV p27 core antigen protein amplified by gag specific primers. Lane 3 illustrates the absence of the specific amplified DNA from non-infected control cells, and Lanes 4–7 show the result of PCR assay in SIV-infected cells in the absence of NOBA (Lane 4), with 0.1% DMSO (Lane 5) and after preincubation and treatment with 10 μM NOBA (Lane 6) and finally with 20 μM NOBA (Lane 7), which completely abolished the signal for the infectious DNA (compare with FIG. 14A). To rule out the possible artifact that the absence of SIV gag DNA may be due to incomplete DNA extraction technique, we also tested for the ubiquitous β-actin gene as shown in FIG. 15B, where Lane 1 shows a molecular marker (Hind III-digested φX174 DNA), lane 2 is the β-actin segment amplified by β-actin specific primers, and lanes 3–7 are β-actin primer amplification of the DNA extracted from a non-infected cell culture (lane 3) and infected cell cultures treated with 0 μM NOBA (lane 4), 0 μM NOBA with 0.1% DMSO (lane 5), 10 μM NOBA (lane 6), and 20 μM NOBA (lane 7). These results confirm that the absence of the SIV genome in infected cells treated with 20 μM NOBA was not due to the lack of extractable DNA.

In order to identify an AZT-resistant SIV strain, viruses from SIV-infected rhesus macaques were isolated and tested for their resistivity toward AZT. The molecular clone $SIV_{mac}239$ was AZT-sensitive but virus isolates from an $SIV_{mac}239$-infected rhesus macaque (MMU 23740) fourteen months post-infection were AZT resistant; AZT only partially inhibited the growth of SIV 23740 compared to $SIV_{mac}239$, suggesting that the macaque virus contained a mixture of the original infecting virus ($SIV_{mac}239$) and other, mutated viruses. A comparison of the number of syncytia formed in AZT-treated wells revealed the complete absence of the cytopathic effect of $SIV_{mac}239$ in contrast to SIV 23740 (Table V).

TABLE V

The effect of AZT on nonresistant and AZT-resistant $SIV_{mac}$ as assayed by syncytia formation

| Virus | AZT concentration (μM) | Syncytia[b] |
|---|---|---|
| $SIV_{mac}$ 239 | 0 | ++++ |
|  | 10 | – |
|  | 15 | – |
|  | 20 | – |
|  | 25 | – |
|  | 30 | – |

TABLE V-continued

The effect of AZT on nonresistant and AZT-resistant SIV$_{mac}$ as assayed by syncytia formation

| Virus | AZT concentration (μM) | Syncytia[b] |
|---|---|---|
| | 35 | − |
| | 40 | − |
| SIV 23740 | 0 | ++++ |
| (AZT-resistant) | 10 | ++++ |
| | 15 | ++++ |
| | 20 | ++++ |
| | 25 | ++++ |
| | 30 | ++++ |
| | 35 | ++++ |
| | 40 | ++++ |

[a]CEM x174 cells (1.5 × 10$^5$/500 ul) were infected with equal doses of SIV$_{mac}$ 239 or virus isolates from an SIV$_{mac}$ 239-infected rhesus macaque (MMU 23740). Three days post-infection, AZT concentrations ranging from 0 to 40 μM were added to the cells and the cultures were incubated for four days. The wells were replenished with fresh CEM x174 cells and AZT and incubated for an additional three days. Cell cultures were then examined for syncytia formation.
[b]The number of syncytia in cell cultures was counted in arbitrary fields under 60× magnification and scored as follows: over 30 (++++), 20–30 (+++), 10–20 (++), 1–9 (+), and 0 (−).

Figure 16A:
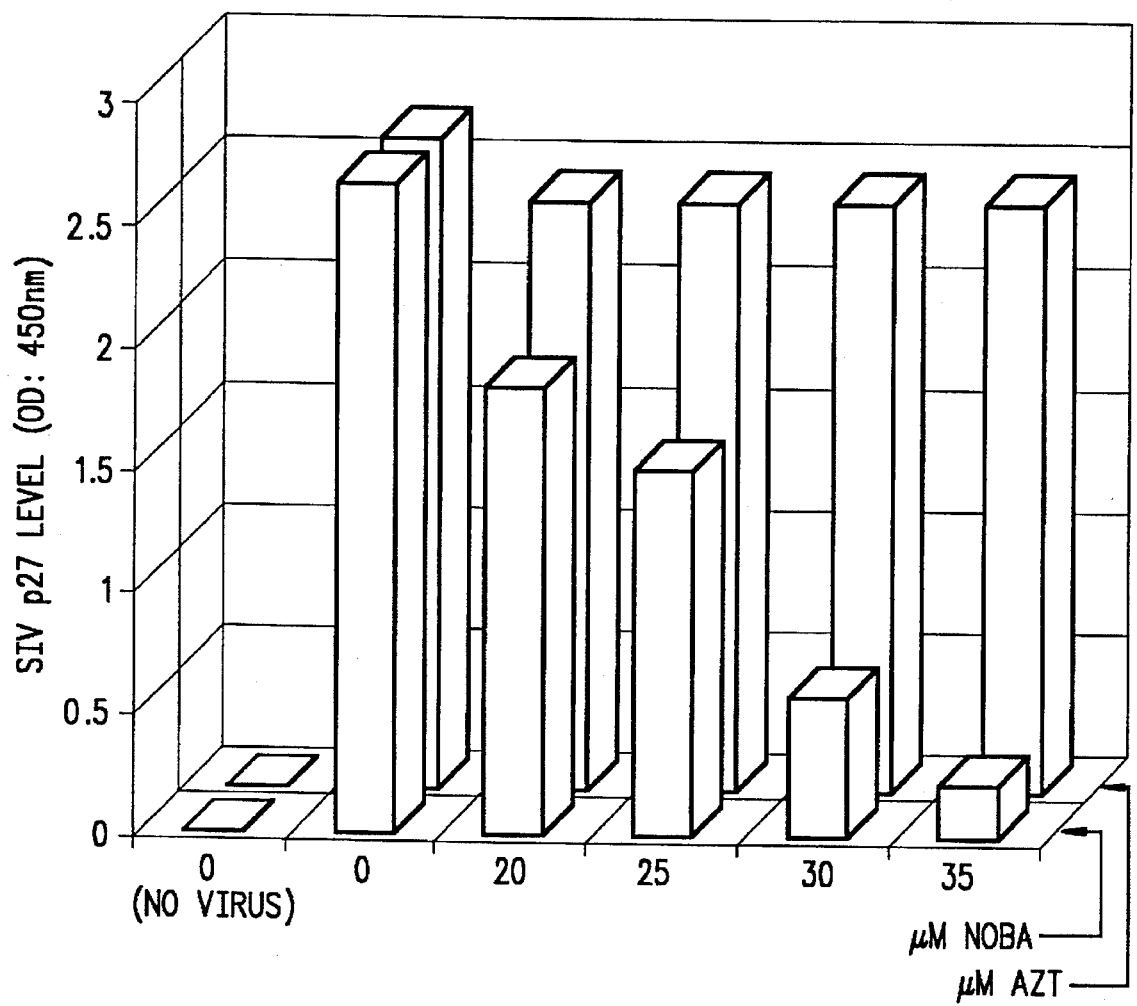
FIGS. 16A–B. Effect of NOBA on AZT-resistant strains of SIV. Peripheral blood mononuclear cells ($1.2 \times 10^6$) from an $SIV_{mac}239$-infected rhesus macaque (MMU23740) were co-cultivated in a 24-well tissue culture plate with $3 \times 10^5$ CEM x174 cells/ml for 6 days. Alquots (500 ul) of the co-cultivation supernatant were added to $3 \times 10^5$ fresh CEM x174 cells/ml. The cells were incubated at 37° C. for another 2 days (until syncytia appeared) before adding NOBA or AZT. Cultures were replenished with new medium containing drug on day 9. Fresh CEM x174 cells ($1.75 \times 10^5$/well) and drug were added on day 13.
Figure 16B:
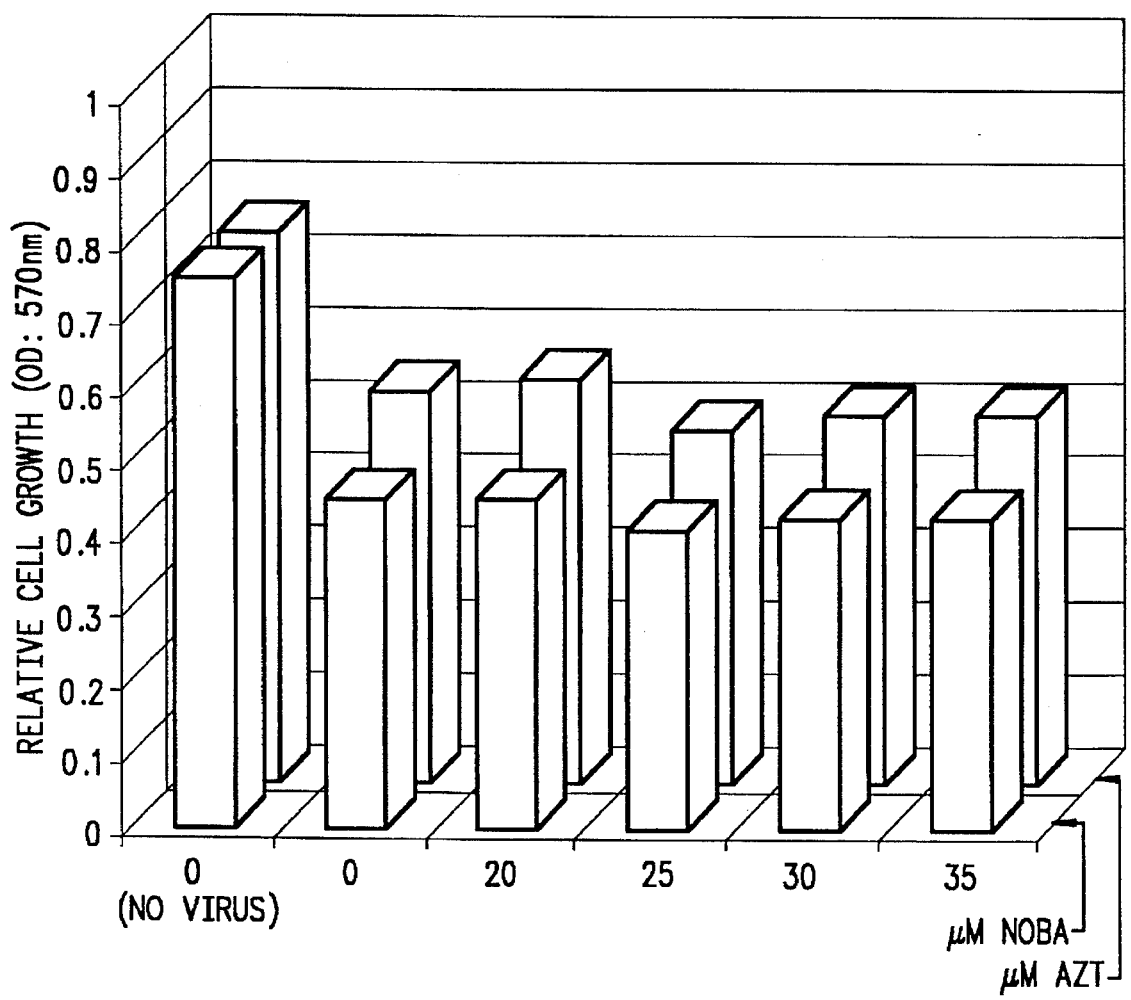

The inhibitory action of NOBA on the replication of AZT-resistant SIV strains was assayed by incubating supernatants of 6-day-old co-cultivation systems, consisting of MMU23740 PBMCs and CEM x174, with fresh CME x174 cells. This system simulates conditions that may exist in vivo. Assays for the p27 core antigen with ELISA 16 days after the initial co-cultivation showed a NOBA does-dependent depression of SIV 23740 production, whereas no antiviral action of AZT occurred (FIG. 16A). There was no significant drug-dependent decrease of cell activity due to either NOBA or AZT (FIG. 16B).

In contrast to the powerful anti-SIV action of NOBA, no direct effect on reverse transcriptase activity could be ascertained (Table VI)

TABLE VI $^3$H-TPP incorporation by SIV 239-RT in the presence of NOBA[a]

| Concentration of NOBA (μM) | cpm (× 10$^3$) |
|---|---|
| 0 (no enzyme) | 0.4 |
| 0 | 761.4 |
| 0 (0.1% DMSO) | 743.8 |
| 0.8 | 897.0 |
| 20.0 | 763.8 |
| 40.0 | 748.8 |
| 80 | 764.9 |
| 400.0 | 690.7 |
| 800.0 | 706.6 |

[a]Reverse transcriptase assays were performed with DMSO controls in the presence or absence of NOBA.

Figure 17:
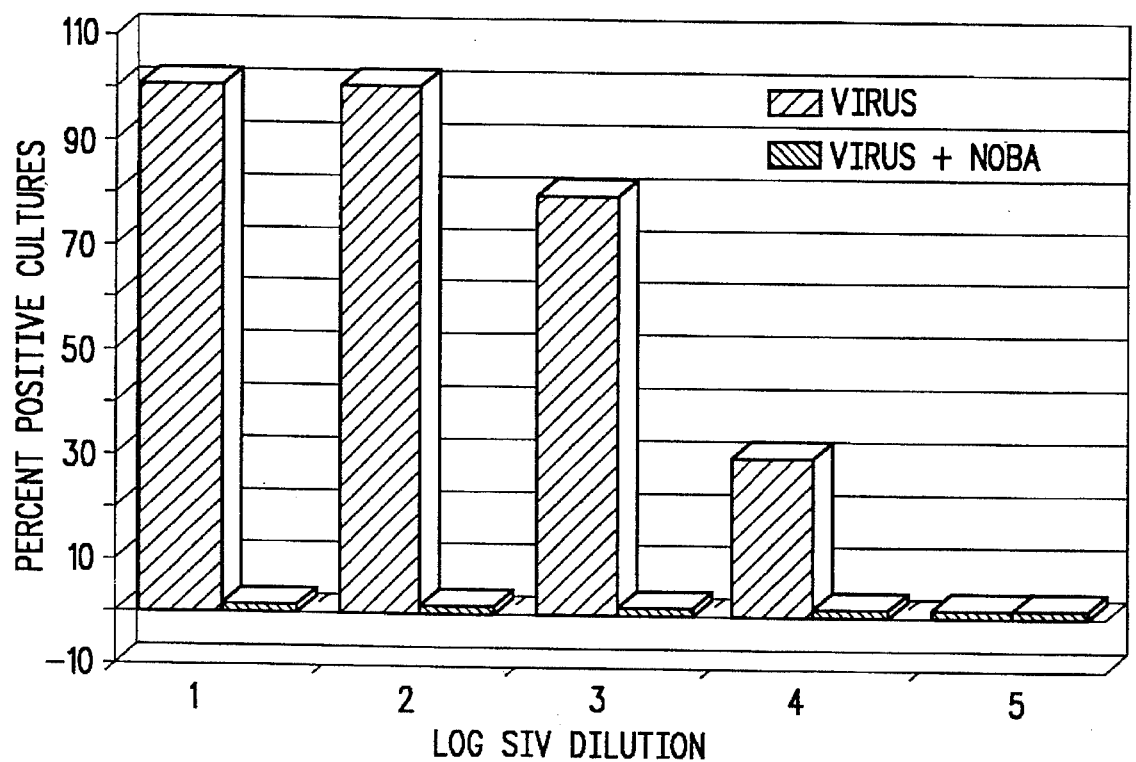
FIG. 17. The effect of NOBA on SIV assayed in human lymphocytes. A concentrated stock of $SIV_{sum}$ ($TCID_{50}$= 3300) was incubated 30 min at 37° C. with 50 µM NOBA. Afterwards, the mixture was serial 10-fold diluted to yield the $10^{-1}$, $10^{-2}$, $10^{-3}$, $10^{-4}$ and $10^{-5}$ dilutions. Each dilution was used to infect $10^6$ PHA-PBL for 18 hrs at 37° C. after which the free virus and drug were removed. Cells were then aliquoted into 96 well plates ($10^5$ cells/well with 10 replicates per dilution). Cultures were scored positive for infection if their absorbance at 490 nm in the antigen capture ELISA was >3 S.D. above the mean absorbance 10 uninfected cultures. The untreated virus (□) scored positive cultures with dilutions as low as $10^{-4}$, whereas NOBA-treated virus □ did not score positive with any cultures.

The direct anti-SIV action of NOBA was also assayed with human peripheral lymphocytes that were stimulated by phytohemagglutinin (PHA-PBL) as described for HIV in Example XIII. This experiment represents a direct comparison between SIV and HIV in the same test system. As seen in FIG. 17, preincubation of SIV$_{smm}$ with 50 μM NOBA for 30 min at 37° C. completely suppressed SIV replication in PHA-PBL. As determined in separate studies, designed to quantitate the dose-responsive effect of NOBA on SIV replication in PBMCs, the EC$_{50}$ value (concentration of drug that suppresses 50% virus replication) varied between 17 and 8 μM NOBA for SIV$_{smm}$ and SIV$_{smbi}$ strains, respectively.

XV. The Site of Antiviral Action of 3-nitrosobenzamide on the Infectivity Process of HIV in Human Lymphocytes

Virus Replication Inhibition Assays

Phytohemagglutinin-stimulated human peripheral blood mononuclear cells (PBMC) were distributed into 96-well plates (10$^5$/well) in the presence of indicated concentrations of NOBA and 250 TCID$_{50}$ of the HIV-1$_{WeJo}$ pediatric clinical isolate that has been propagated only in human PBMC. After 7 days, cultures were assayed for p24 antigen content using a p24 antigen-capture kit (Coulter Immunology, Hialeah, Fla.). Cell viability was quantitated using biscarboxyethyl-5(6)-carboxyfluorescein acetoxymethyl ester (BCECF, Molecular Probes, Inc., Eugene, Ore.) as previously described. Gulakowski et al., J. Virol Methods 40: 347–356 (1991).

Enzyme Assays

The in vivo activity of RT was determined with the Boehringer Mannheim ELISA kit and 3'-azido-3'-deoxythymidine-5'-triphosphate (AZTTP) was included as a positive control for inhibition of RT. For the endogenous reverse transcription assay, 10 μg of virus HIV-1$_{IIIB}$ (Universal Biotechnology Inc., Rockville, Md.) were treated with NOBA at indicated concentrations for 10 min at 25° C., followed by permeabilization of the virus with melittin (Sigma Chemical Co., St. Louis, Mo.) and subsequent incubation of the reaction mixture for 6 hrs at 39° C. as previously described. Yong et al., AIDS 4: 199–206 (1990). Reactions were terminated with 0.1% SDS/10 mM EDTA, and electrophoresis performed on 0.7% agarose gels, the gels dried and exposed to autoradiography. HIV-1 protease activity was quantitated by a reverse phase HPLC assay as previously described (Wondrak et al., FEBS Lett 280: 347–350 (1991)) and HIV-1 integrase activity was measured as reported (Fesen et al., P.N.A.S. 90: 2399–2403 (1993)). For comparison, topoisomerase I and II were assayed as described (Jaxel et al., J. Biol. Chem. 266: 20418–20423 (1991)).

DNA Amplification Procedures

Proviral DNA synthesis was monitored with an undiluted HIV-1$_{IIIB}$ stock that had been premixed with NOBA or the DMSO solvent and to this mixture 3×10$^6$ PBMC were added and cultured for 24 hrs. Cells were then washed and the DNA extracted and PCR-amplified with LTR/gag primer pairs (M667/M661) and the products analyzed by 2% agarose gels which were visualized by autoradiography of the dried gels, as previously described (Zack et al., Cell 61: 213–222 (1990)).

Virus Attachment Assays

Binding of HIV-1$_{RF}$ to PBMC was measured by a p24-based assay. Briefly, 5×10$^5$ PBMC were incubated with a concentrated stock of virus for 30 min, the unbound virus washed away, and the cell-associated virus solubilized and analyzed by the p24 antigen-capture assay. The binding of HIV-1 to PBMCs was blocked in a concentration-dependent manner by destran sulfate (see Table VII. Cell surface binding of HIV-1$_{LAV}$ to PBMC was also quantitated by flow cytometry using FITC-anti-HIV-1$_{LAV}$ as reported McDougal et al., J. Immunol. 135: 3151–3162 (1985).

The 3-Nitrosobenzamide was synthesized as described in Example II.

Inhibitory Effect of NOBAS on Viral Replication

Figure 18:
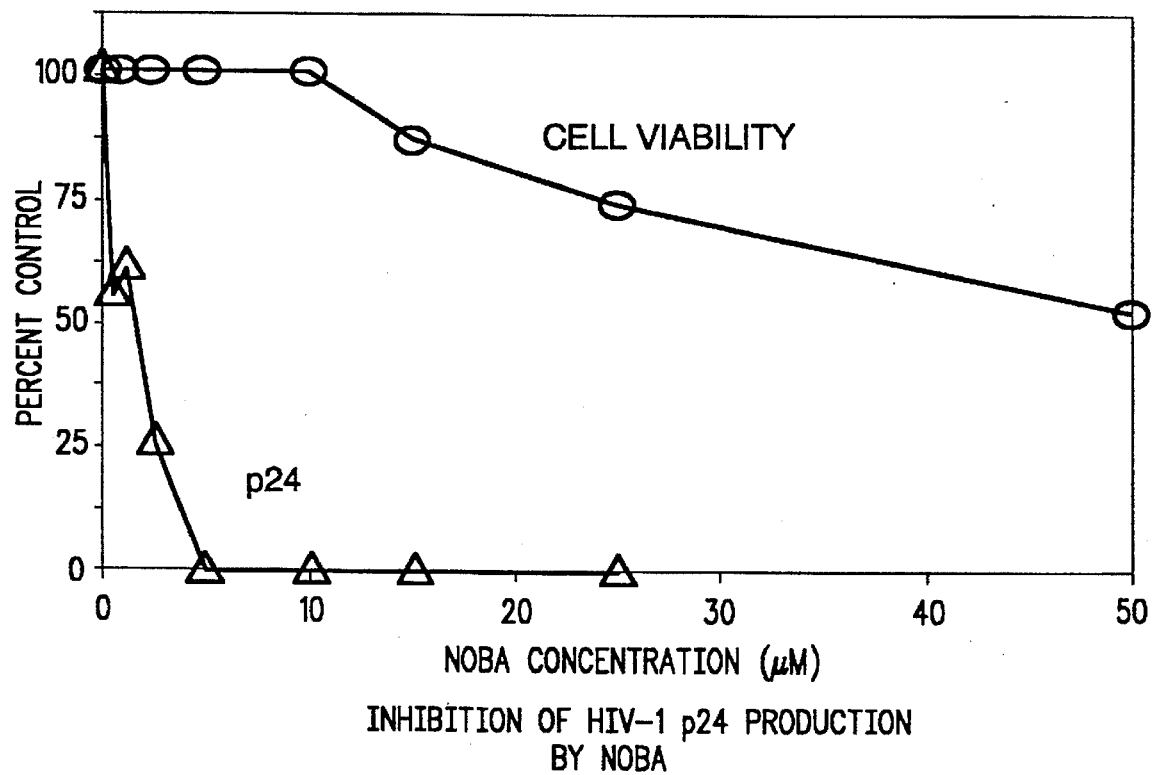
FIG. 18. Inhibition of HIV-$1_{WeJo}$ replication by NOBA. Human PBMC were aliquoted into 96-well plates ($10^5$/well) and various amounts of NOBA were added, immediately followed by the addition of 250 $TCID_{50}$ of HIV-$1_{WeJo}$, and then cultured for 7 days. Virus production was measured by p24 antigen capture (-▲-) and is expressed as the percent of antigen in the infected cells in the absence of drug (10 replicates per point). Cell viability (-■-) was determined by the BCECF assay and activities are expressed as a percentage of the signal in the drug-free and virus-free control (10 replicates per point).

The p7NC protein (nucleocapsid protein of HIV-1 contains two separate zinc fingers sequences that are required not only for packaging of viral genomic RNA but also for early events in viral replication, suggesting that NOBA may induce a specific inhibitory effect in early stages of viral infection. To define this antiviral effect, studies were designed to measure the concentration-dependent action of the drug on HIV-1 replication under conditions in which the target cells (PBMC) were simultaneously mixed with the HIV-1$_{WeJo}$ pediatric clinical isolate and various concentrations of NOBA. As shown in FIG. 18, NOBA inhibited p24 viral antigen production with an $EC_{50}$ (level of drug that inhibits infection by 50%) of 1.56 μM and there is a depression of lymphocytes at 50 μM NOBA. Since the in vitro culturing of lymphocytes requires phytohemagglutinin, necessarily introducing some degree of artificiality, in vitro efficacy of NOBA has to be studied in cell types that need no artificial growth stimulants. For these reasons the apparent efficacy of NOBA, estimated to be about 32, in stimulated lymphocytes may be an underestimation.

Figure 19:
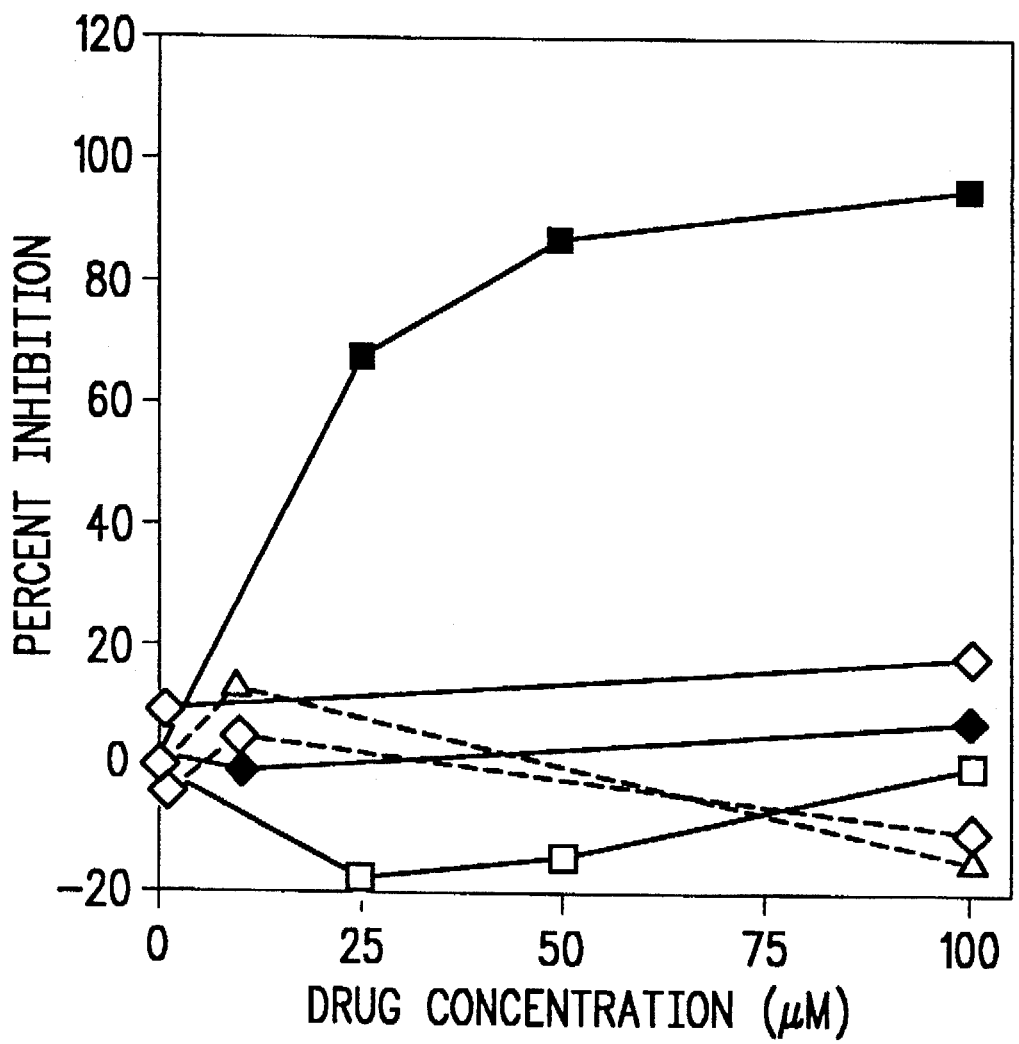
FIG. 19. HIV-1 Intergrase protein (2 picomoles/reaction) produced via an *E. coli.* expression vector was stored at −70° C. in 1M NaCl, 20 mM HEPES (pH 7.6), 1 mM EDTA, 1 mM dithiorhreitol, and 20% glycerol (W/V). -◇-NOBA, preincubation, DNA cleavage assay; -▲- NOBA, preincubation, INTEGRATION assay; -◇-NOBA, no preincubation, cleavage assay; - - NOBA, no preincubation, INTEGRATION assay; - - Caffeic acid (phenethylester), no pre-incubation, cleavage assay; -■- Caffeic acid (phenethylester), no -re-incubation, INTEGRATION assay.

Insensitivity of the binding of HIV-1 to cells, and of reverse transcriptase, HIV-1 protease and integrase to NOBA. The influence of NOBA on the binding of HIV-1 to PBMC and on the in vitro activities of HIV-1 namely on reverse transcriptase (RT), protease (PR) and integrase (IN) was determined. Pretreatment of virus with 100 μM NOBA had no effect on the attachment of virus, as quantitated by the association of p24 with the PBMC (Table VI), whereas 10 μg/ml dextran sulfate produced nearly complete inhibition. The lack of an effect on viral attachment by C-nitroso drugs was also confirmed by a flow cytometry method which is based on the FITC-anti-HIV-1 assay (not shown). Employing an artificial homopolymer template-primer, (poly(rA).oligo(dT)), there was no inhibitory effect of NOBA on the activity of RT (see Table VI), while 3-azido-3'-deoxythymidine-5'-triphosphate (AZTTP) effectively inhibited RT activity. Likewise, although the A-74704 synthetic PR inhibitor (Chow et al., Nature 361: 560–564 (1993)) depressed PR at a concentration of 1 μM, NOBA (100 μM) demonstrated no inhibition of PR activity (Table I). It is of particular interest that NOBA had no effect on IN activity (FIG. 19) even after preincubation. This protein contains a "classical" type of zinc finger sequence (CCHH rather than the retroviral CCHC type) Khan et al., Nucleic Acids Research 19: 851–860 (1991). As a positive control, the inhibitory action of caffeic acid (phenethylester) on IN is also shown. Since the major DNA binding nuclear enzymes, topoisomerase I & II, contain zinc, the action of NOBA was also tested on these enzymes. At concentrations of NOBA which completely block HIV infectivity or the formation of proviral DNA, no effects on topo I and II could be ascertained even after preincubation for one hour (FIG. 19). Thus, NOBA was without effect on four major targets of HIV-1 (attachment, RT, PR and IN) and exhibited specificity towards the retroviral zinc finger structure.

Figure 20:
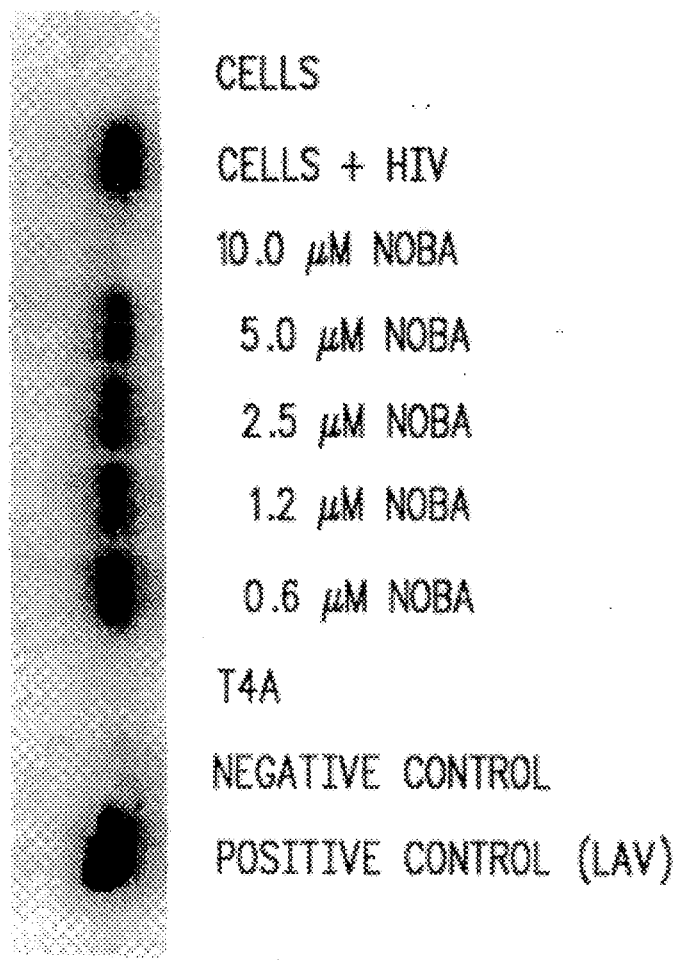
FIG. 20. PCR analysis of the effect of NOBA on HIV-1 proviral DNA formation in PBMC. Various concentrations of NOBA were added to a concentrated stock of HIV-1 (30 min at 37° C.), which was then mixed with a pellet of $3 \times 10^6$ PBMC and incubated for 24 hours. The concentration of drug in the final mixture is indicated. After incubation the samples were analyzed by PCR as described in Materials and Methods. As a control, cells were exposed to virus in the presence of anti-T4 monoclonal antibodies (T4A) to block infection. The negative control represents the PCR reaction performed in the absence of primers. The positive control is the 8E5 bone marrow isolate from a patient infected with HIV-1$_{LAV}$.
Figure 21:
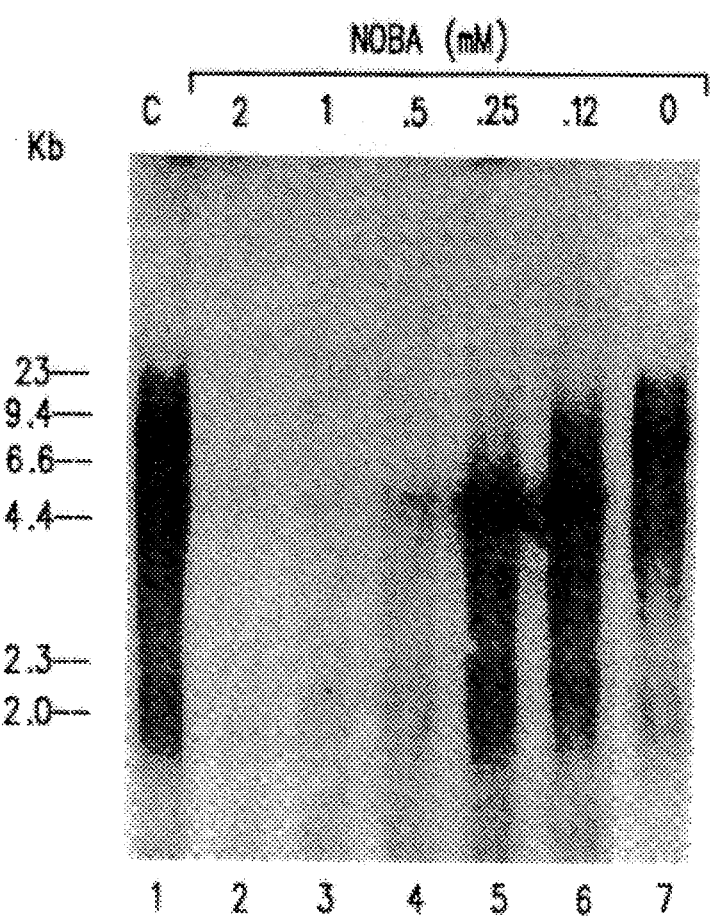
FIG. 21. Inhibition of endogenous reverse transcription in HIV-1 virions by NOBA. Permeabilized HIV-1 virions were allowed to reverse transcribe their native RNA to viral DNA in the absence or presence of various concentrations of NOBA. The controls were virus alone (C) or virus in the presence of 1% DMSO (0 drug). The [$^{32}$P]-dCTP labeled transcripts were viewed by autoradiography on 1% gels.

NOBA blocks the synthesis of proviral DNA. The formation of proviral DNA within PBMC was determined by mixing a concentrated stock suspension of HIV-1$_{LAV}$ with the drug followed by addition to PBMC cultures. After 24 hrs. in culture the cells were analyzed by the PCR methodology with LTR/gag (M667/M661) primer pairs to probe for the presence of full-length or nearly full-length proviral DNA Zack et al., Cell 61: 213–222 (1990). The products of reverse transcription, as assayed by PCR, were completely blocked by 10 μM NOBA (FIG. 20). Virus replication was also blocked under the same conditions (not shown). There was inhibition of the reverse transcription process by NOBA when assayed in permeabilized HIV-1 virions (FIG. 21) composed of the native RNA template, tRNA$^{lys,3}$ primer, RT and NC proteins. This "endogenous" assay contained a 100-fold higher concentrated stock of HIV-1$_{IIIB}$ than the tests illustrated in FIG. 20, therefore higher concentrations of NOBA were required, since there is a stoichiometry between the concentration of NOBA and that of retroviral zinc fingers. See Example X. Even though NOBA does not directly affect the RT enzyme, it prevents the formation of mature proviral DNA that is required for integration into the cellular genomic DNA.

TABLE VI

Effect of NOBA on Various HIV-1 Functions

| Condition Activity[c] | Attachment[a] | RT Activity[b] | PR |
|---|---|---|---|
| No Drug | 1.01 ± 0.09 | 1.002 ± 0.108 | 0.335 ± 0.129 |
| 100 μM NOBA | 1.17 ± 0.22 | 1.109 ± 0.037 | 0.375 ± 0.147 |
| 10 μg/ml Dex. Sulf | 0.06 ± 0.05 | | |
| 1 μM AZTTP | | 0.087 ± 0.058 | |
| 1 μM A-74704 | | | 0.005 ± 0.01 |

[a]Values for virus attachment (mean ± sd, n = 3 of the absorbance at 450–650 nm) represent p24 levels, as measured by an antigen-capture assay.
[b]HIV-1 RT activities as the mean ± sd (n = 3) of the absorbance (405 nm/490 nm).
[c]Values represent the mean ± sd (n = 3) of the change in absorbance at 206 nm for the cleavage of the HIV-1 PR synthetic substrate.

All publications, patents, and patent applications cited above are herein incorporated by reference.

The foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

What is claimed is:

1. A method of inactivating a virus having a $Zn^{+2}$ finger nucleocapsid protein, said method comprising administering an effective amount of a $Zn^{+2}$ finger destabilizing compound wherein said compound is selected from the group consisting of a compound having the formula:

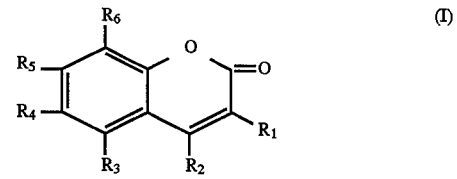

(I)

wherein $R_1$, $R_2$, $R_3$, $R_4$, $R_5$ and $R_6$ are selected from the group consisting of hydrogen and nitroso, and only one of $R_1$, $R_2$, $R_3$, $R_4$, $R_5$ and $R_6$ is a nitroso group, a compound having the formula:

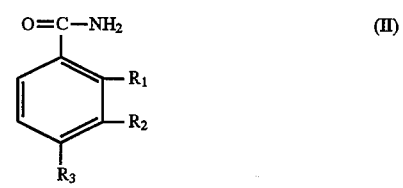

(II)

wherein $R_1$, $R_2$, and $R_3$ are selected from the group consisting of hydrogen and nitroso, and only one of $R_1$, $R_2$, and $R_3$ is a nitroso group, and a a compound having the formula:

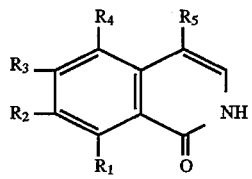

wherein $R_1$, $R_2$, $R_3$, $R_4$, and $R_5$ are selected from the group consisting of hydrogen and nitroso, and only one of $R_1$, $R_2$, $R_3$, $R_4$, and $R_5$ is a nitroso group.

2. A method according to claim 1, wherein said compound is selected from the group consisting of 6-nitroso-1,2-benzopyrone, 3-nitrosobenzamide, 5-nitroso-1(2H)-isoquinolinone, 7-nitroso-1(2H)-isoquinolinone, and 8-nitroso-1(2H)-isoquinolinone.

3. A method according to claim 2, wherein said compound is 3-nitrosobenzamide.

4. A method according to claim 1 wherein said virus is a retrovirus.

5. A method according to claim 4 wherein said retrovirus is HIV-1.

6. A composition comprising a biological material and a compound that destabilizes a $Zn^{+2}$ finger on a viral nucleocapsid protein wherein said biological material is blood and wherein said compound is selected from the group consisting of a compound having the formula:

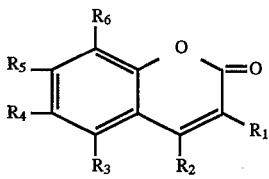

wherein $R_1$, $R_2$, $R_3$, $R_4$, $R_5$ and $R_6$ are selected from the group consisting of hydrogen and nitroso, and only one of $R_1$, $R_2$, $R_3$, $R_4$, $R_5$ and $R_6$ is a nitroso group, a compound having the formula:

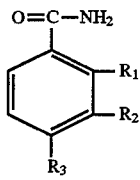

wherein $R_1$, $R_2$, and $R_3$ are selected from the group consisting of hydrogen and nitroso, and only one of $R_1$, $R_2$, and $R_3$ is a nitroso group, and a a compound having the formula:

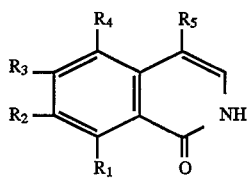

wherein $R_1$, $R_2$, $R_3$, $R_4$, and $R_5$ are selected from the group consisting of hydrogen and nitroso, and only one of $R_1$, $R_2$, $R_3$, $R_4$, and $R_5$ is a nitroso group.

7. A composition according to claim 6, wherein said compound is 3-nitrosobenzamide.

8. A method for treating retroviral infections, said method comprising the step of administering an effective amount of a compound selected from the group consisting of:

a compound having the formula:

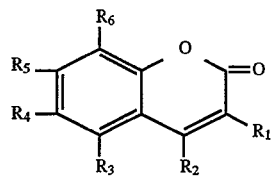

wherein $R_1$, $R_2$, $R_3$, $R_4$, $R_5$ and $R_6$ are selected from the group consisting of hydrogen and nitroso, and only one of $R_1$, $R_2$, $R_3$, $R_4$, $R_5$ and $R_6$ is a nitroso group, a compound having the formula:

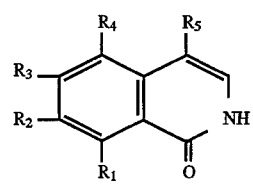

wherein $R_1$, $R_2$, $R_3$, $R_4$, and $R_5$ are selected from the group consisting of hydrogen and nitroso, and only one of $R_1$, $R_2$, $R_3$, $R_4$, and $R_5$ is a nitroso group, and a compound having the formula:

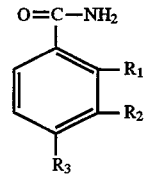

wherein $R_1$, $R_2$, and $R_3$ are selected from the group consisting of hydrogen and nitroso, and only one of $R_1$, $R_2$, and $R_3$ is a nitroso group.

9. A method according to claim 8, wherein said compound is selected from the group consisting of 6-nitroso-1,2-benzopyrone, 3-nitrosobenzamide, 5-nitroso-1(2H)-isoquinolinone, 7-nitroso-1(2H)-isoquinolinone, and 8-nitroso-1(2H)-isoquinolinone.

10. A method according to claim 8, wherein said compound is 3-nitrosobenzamide.

11. A method according to claim 8 wherein said retroviral infection is an HIV infection.

12. A composition for the treatment of retroviral diseases, said composition comprising a compound according to claim 8.

13. A pharmaceutical composition for the treatment of retroviral diseases, said composition comprising a pharmaceutically effective amount of a compound according to claim 8.

14. A composition for the treatment of HIV infections, said composition comprising a compound according to claim 8.

15. A method of inactivating an AZT resistant virus, said method comprising administering a pharmaceutically effective amount of a nitroso compound wherein said compound is selected from the group consisting of a compound having the formula:

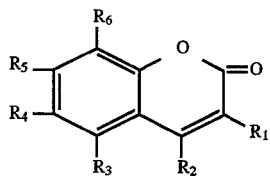

wherein $R_1$, $R_2$, $R_3$, $R_4$, $R_5$ and $R_6$ are selected from the group consisting of hydrogen and nitroso, and only one of $R_1$, $R_2$, $R_3$, $R_4$, $R_5$ and $R_6$ is a nitroso group, a compound having the formula:

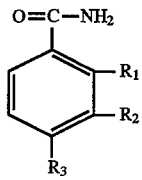

wherein $R_1$, $R_2$, and $R_3$ are selected from the group consisting of hydrogen and nitroso, and only one of $R_1$, $R_2$, and $R_3$ is a nitroso group, and a a compound having the formula:

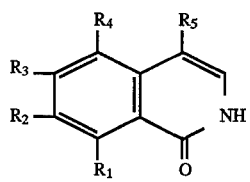

wherein $R_1$, $R_2$, $R_3$, $R_4$, and $R_5$ are selected from the group consisting of hydrogen and nitroso, and only one of $R_1$, $R_2$, $R_3$, $R_4$, and $R_5$ is a nitroso group.

16. A method according to claim 15, wherein said compound is selected from the group consisting of 6-nitroso-1, 2-benzopyrone, 3-nitrosobenzamide, 5-nitroso-1(2H)-isoquinolinone, 7-nitroso-1(2H)-isoquinolinone, and 8-nitroso-1(2H)-isoquinolinone.

17. A method according to claim 16, wherein said compound is 3-nitrosobenzamide.

18. A method according to claim 17 wherein said virus is a retrovirus.

19. A method according to claim 18 wherein said retrovirus is HIV.

20. A method of reducing the level of integrated viral DNA from the genome of a host, said method comprising administering a pharmaceutically effective amount of a nitroso compound wherein said compound is selected from the group consisting of a compound having the formula:

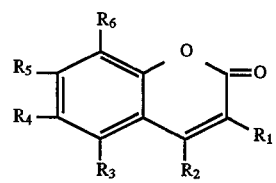

wherein $R_1$, $R_2$, $R_3$, $R_4$, $R_5$ and $R_6$ are selected from the group consisting of hydrogen and nitroso, and only one of $R_1$, $R_2$, $R_3$, $R_4$, $R_5$ and $R_6$ is a nitroso group, a compound having the formula:

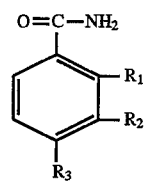

wherein $R_1$, $R_2$, and $R_3$ are selected from the group consisting of hydrogen and nitroso, and only one of $R_1$, $R_2$, and $R_3$ is a nitroso group, and a a compound having the formula:

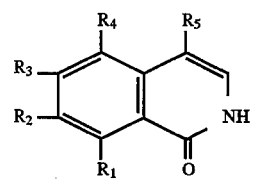

wherein $R_1$, $R_2$, $R_3$, $R_5$, and $R_6$ are selected from the group consisting of hydrogen and nitroso, and only one of $R_1$, $R_2$, $R_3$, $R_4$, and $R_5$ is a nitroso group.

21. A method according to claim 20, wherein said compound is selected from the group consisting of 6-nitroso-1, 2-benzopyrone, 3-nitrosobenzamide, 5-nitroso-1(2H)-isoquinolinone, 7-nitroso-1(2H)-isoquinolinone, and 8-nitroso-1(2H)-isoquinolinone.

22. A method according to claim 21, wherein said compound is 3-nitrosobenzamide.

23. A method according to claim 22 wherein said virus is a retrovirus.

24. A method according to claim 23 wherein said retrovirus is HIV.

* * * * *